(12) United States Patent
Rabbani et al.

(10) Patent No.: US 7,064,197 B1
(45) Date of Patent: *Jun. 20, 2006

(54) SYSTEM, ARRAY AND NON-POROUS SOLID SUPPORT COMPRISING FIXED OR IMMOBILIZED NUCLEIC ACIDS

(75) Inventors: Elazar Rabbani, New York, NY (US); Jannis G. Stavrianopoulos, Bayshore, NY (US); Dollie Kirtikar, Fresh Meadows, NY (US); Kenneth H. Johnston, New Orleans, LA (US); Barbara E. Thalenfeld, New York, NY (US)

(73) Assignee: Enzo Life Sciences, Inc. c/o Enzo Biochem, Inc., Farmingdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/486,070

(22) Filed: Jun. 7, 1995

Related U.S. Application Data

(63) Continuation of application No. 07/967,646, filed on Oct. 28, 1992, now abandoned, which is a continuation of application No. 07/607,347, filed on Oct. 30, 1990, now abandoned, which is a continuation of application No. 07/385,986, filed on Jul. 20, 1989, now Pat. No. 4,994,373, which is a continuation of application No. 06/732,374, filed on May 9, 1985, now abandoned, which is a continuation-in-part of application No. 06/461,469, filed on Jan. 27, 1983, now abandoned.

(51) Int. Cl.
*C07H 21/04* (2006.01)
*C12N 16/11* (2006.01)

(52) U.S. Cl. .................... 536/24.3; 536/25.32
(58) Field of Classification Search .................... 435/6, 435/287, 810, 283.1, 285.1, 287.1, 287.2, 435/287.7, 287.9, 288.7, 289.1, 297.1, 299.1; 436/501; 536/22.1; 935/78, 77, 88; 422/50, 422/55, 56, 57, 68.1, 69, 82.05, 82.06, 82.07, 422/82.08
See application file for complete search history.

(56) References Cited

U.S. PATENT DOCUMENTS

| | | | |
|---|---|---|---|
| 3,669,841 A | 6/1972 | Miller | 195/63 |
| 3,715,278 A | 2/1973 | Miller | 195/63 |
| 3,849,137 A | 11/1974 | Barzynski | |
| 3,949,064 A | 4/1976 | Bornstein et al. | 424/1 |
| 4,001,583 A | 1/1977 | Barrett | 250/303 |
| 4,041,146 A | 8/1977 | Giaever | 424/1 |
| 4,059,685 A | 11/1977 | Johnson | 424/12 |
| 4,106,907 A | 8/1978 | Charlton et al. | |
| 4,116,638 A | 9/1978 | Kenoff | 422/99 |
| 4,120,945 A | 10/1978 | Gutcho et al. | 424/1 |
| 4,134,792 A | 1/1979 | Boguslaski et al. | 195/99 |
| 4,166,103 A | 8/1979 | Wagner et al. | 424/1 |
| 4,166,104 A | 8/1979 | Wagner et al. | 424/1 |
| 4,228,237 A | 10/1980 | Hevey et al. | 435/7 |
| 4,230,797 A | 10/1980 | Boguslaski et al. | 435/7 |
| 4,234,563 A | 11/1980 | Rippe | |
| 4,234,681 A | 11/1980 | DeLuca-McElroy | 435/8 |
| 4,251,514 A | 2/1981 | Rippe | |
| 4,254,097 A | 3/1981 | Rippe | |
| 4,261,893 A | 4/1981 | Boguslaski et al. | 260/326 |
| 4,269,933 A | 5/1981 | Pazos | |
| 4,271,140 A | 6/1981 | Bunting | 424/1 |
| 4,280,992 A | 7/1981 | Sugiura et al. | 424/1 |
| 4,302,204 A | 11/1981 | Wahl et al. | 23/230.3 |
| 4,312,944 A | 1/1982 | Mattiasson et al. | 435/7 |
| 4,318,980 A | 3/1982 | Boguslaski et al. | 435/7 |
| 4,318,981 A | 3/1982 | Burd et al. | 435/7 |
| 4,318,982 A | 3/1982 | Hornby et al. | 435/7 |
| 4,358,535 A | 11/1982 | Falkow et al. | 435/5 |
| 4,374,925 A | 2/1983 | Litman et al. | 435/7 |
| 4,376,110 A | 3/1983 | David et al. | 436/513 |
| 4,380,580 A | 4/1983 | Boguslaski et al. | 435/7 |
| 4,383,031 A | 5/1983 | Boguslaski et al. | 435/7 |
| 4,391,904 A | 7/1983 | Litman et al. | 435/7 |
| 4,446,231 A | 5/1984 | Self | 435/7 |
| 4,483,920 A | 11/1984 | Gillespie et al. | 435/6 |
| 4,486,539 A | 12/1984 | Ranki et al. | 436/504 |
| 4,516,833 A | 5/1985 | Fusek | |
| 4,517,338 A | 5/1985 | Urdea | |
| 4,537,861 A | 8/1985 | Elings | |

(Continued)

FOREIGN PATENT DOCUMENTS

DE P2618419 4/1976

(Continued)

OTHER PUBLICATIONS

Manuelidis et al. (1982) Journal of Cell Biology, vol. 95, pp. 619-625.*

(Continued)

*Primary Examiner*—John S. Brusca
(74) *Attorney, Agent, or Firm*—Ronald C. Fedus

(57) ABSTRACT

Nucleic acids are fixed or immobilized to non-porous solid supports (substrates), and include systems containing such supports and arrays with fixed or immobilized nucleic acids. These compositions are useful for nucleic acid analyses and a host of applications, including, for example, detection, mutational analysis and quantification. The non-porous solid supports can be transparent or translucent, and the surfaces can be treated with agents to fix or immobilize the nucleic acids. Such agents include, for example, amine providing compounds, epoxy compounds and acid solutions. The fixed or immobilized nucleic acids can be unlabeled, or labeled with at least one non-radioactive signaling moiety, such as the case when the nucleic acids are double-stranded.

238 Claims, No Drawings

U.S. PATENT DOCUMENTS

| | | | |
|---|---|---|---|
| 4,542,102 A | 9/1985 | Dattagupta | |
| 4,562,157 A | 12/1985 | Lowe | |
| 4,563,419 A | 1/1986 | Ranki et al. | 435/6 |
| 4,581,333 A | 4/1986 | Kourilsky et al. | 435/6 |
| 4,358,535 A | 5/1986 | Falkow et al. | |
| 4,656,127 A | 4/1987 | Mundy | |
| 4,689,405 A | 8/1987 | Frank | |
| 4,711,955 A | 12/1987 | Ward et al. | 536/29 |
| 4,713,326 A | 12/1987 | Dattagupta | |
| 4,724,202 A | 2/1988 | Dattagupta et al. | 435/6 |
| 4,732,847 A * | 3/1988 | Stuart et al. | 435/6 |
| 4,824,776 A | 4/1989 | Heller | 435/6 |
| 4,973,493 A | 11/1990 | Guire | |
| 4,994,373 A * | 2/1991 | Stavrianopoulos et al. | 435/6 |
| 5,098,825 A | 3/1992 | Tchen et al. | |
| 5,241,060 A | 8/1993 | Engelhardt et al. | 536/27 |
| 5,260,433 A | 11/1993 | Engelhardt et al. | 536/23.1 |
| 5,328,824 A | 7/1994 | Ward et al. | 435/6 |
| 5,449,767 A | 9/1995 | Ward et al. | 563/6 |
| 5,476,928 A | 12/1995 | Ward et al. | 536/24 |

FOREIGN PATENT DOCUMENTS

| | | |
|---|---|---|
| DE | A2724486 | 12/1977 |
| DE | 2915082 | 10/1979 |
| DE | A2915082 | 10/1979 |
| EP | 0046083 | 2/1982 |
| EP | 0 070 687 | 7/1982 |
| EP | 0063879 B1 | 11/1982 |
| EP | 0070685 | 1/1983 |
| EP | 0070687 | 1/1983 |
| EP | 0097373 B1 | 1/1984 |
| EP | 0103197 | 3/1984 |
| GB | 1548741 | 7/1979 |
| GB | A2014727 | 7/1979 |
| GB | 1552607 | 9/1979 |
| GB | 2019408 * | 10/1979 |
| GB | 2019408 A | 10/1979 |
| GB | A2026690 | 2/1980 |
| GB | 2041922 A | 9/1980 |
| GB | 2045239 | 10/1980 |
| GB | 2125946 A | 3/1984 |
| JP | 2825090 | 11/1998 |
| WO | WO 83/02276 | 7/1983 |
| WO | WO 83/02286 | 7/1983 |
| WO | WO 8302277 | 7/1983 |
| WO | WO8403564 | 9/1984 |

OTHER PUBLICATIONS

Langer et al., "Enzymatic Synthesis of Biotin-Labeled Polynucleotides: Novel Nucleic Acid Affinity Probes," *Proc. Natl. Acad. Sci. (USA)*, 78 (11):6633-6637 (Nov. 1981).

Ruth et al., "C-5 Substituted Pyrimidine Nucleosides. 1.Synthesis of C-5 Allyl, Propyl, and Propenyl Uracil and Cytosine Nucleosides via Organopalladium Intermediates," *J. Org. Chem.* 43(14):2870-2876 (1978).

Bergstrom et al., "C-5 Substituted Pyrimidine Nucleosides. 2.Synthesis, via Olefin Coupling to Organopalladium Intermediates Derived from Uridine and 2'-Deoxyuridine," *J. Amer. Chem. Soc.* 100(26):8106-8112 (1978).

Bigge et al., "Palladium-Catalyzed Coupling Reactions of Uracil Nucleosides and Nucleotides," *J. Amer. Chem. Soc.* 102:2033 (1980).

Weetal et al., "Porous Glass for Affinity Chromatography Applications," *Methods in Enzymology*, vol. 34, *Affinity Techniques Enzyme Purification: Part B*, pp. 59-72 (Jakoby, W.B. and Wilchek, M., eds.) (1974).

Filippusson et al., "The Preparation and Properties of Yeast β-Fructofuranosidase," *Biochem J.* 120:215-219 (1970).

Chard T., *An Introduction To Radioimmunoassay And Related Techniques*, Elsevier Science Publishers, B.V. (1978).

Grunstein, M., "Colony Hybridization: A Method For The Isolation of Cloned DNAs That Contain A Specific Gene," *Proc. Natl. Acad. Sci. (USA)* 72:3961-3965 (1975).

Stavrianopoulos et al., "Glycosylated DNA Probes For Hybridization/ Detection of Homologous Sequences," presented at the Third Annual Congress For Recombinant DNA Research (1983).

Singer et al., "Actin Gene Expression Visualized In Chicken Muscle Tissue Culture by Using *In Situ* Hybridization With A Biotinated Nucleotide Analog," *Proc. Nat'l Acad. Sci (USA)* 79:7331-7335 (1982).

Kennell, "Principles and Practices of Nucleic Acid Hybridization," *Progr. Nuc. Acid. Res. Mol. Biol.*, vol. 11, pp. 259-262 (1971).

Alberts et al., *Molecular Biology of the Cell*, Garland Publishers, New York and London (1983), p. 719.

Hood et al., *Immunology*, Benjamin/Cummings Publishing Co., Inc. Menlo Park, CA (1978), p. 142.

Schuurs et al., "Enzyme Immunoassay," *Clinica Chimica Acta 81*:1-40 (1977).

Langer-Sofer et al., "Immunological method for mapping genes on Drosophila polytene chromosomes," *Proc. Natl. Acad. Sci. (USA)* 79:4381-4385 (Jul. 1982).

Guesdon et al., "The Use of Avidin-Biotin Interaction in Immunoenzymatic Techniques," *Journal of Histochemistry and Cytochemistry* 27(8):1131-1139 (1979).

Bauman et al., "A new method for fluorescence microscopical localization of specific DNA sequences by in situ hybridization of fluorochrome-labelled RNA," *Exp. Cell Res.* 128:485-490 (1980).

Avrameas et al., "Enzyme immunoassay for the measurement of antigens using peroxidase conjugates," *Biochemie* 54:837-842 (1972).

John et al., "RNA-DNA Hybrids at the Cytological Level," *Nature 223*: 582-587 (1969).

Benton, W.D. and David, R.W., "Screening Agt recombinant clones by hybridization to single plaques in situ," *Science 196*: 180 (1977).

Leary, Brigati and Ward, "Rapid and sensitive colorimetric method for visualizing biotin-labeled DNA probes hybridized to DNA or RNA immobilized on nitrocellulose: Bio-blots," *Proc. Natl. Acad. Sci (USA)* 80: 4045-4049 (Jul. 1983).

Avrameas and Guilbert," Enzyme-immunoassay for the measurement of antigens using peroxidase conjugates," *Biochimie 54*: 837-842 (1972).

Bauman et al., "Rapid and High Resolution Detection of *in situ* Hybridization to Polytene Chromosomes Using Fluorochrome-Labeled RNA." *Chromosoma (Berl.)* 84: 1-18 (1981).

Bildwell et al., "Enzyme Immunoassays for Viral Diseases," *J. Infectious Disease: 136*: S274-S278 (1977).

Broker et al., "Electron Microscopic Visualization of tRNA genes with Ferritin-Avidin: Biotin Labels," *Nucl. Acids Res.*, 5(2): 363-384 (1978).

Engvall and Perlmann, "Enzyme-linked immunosorbent assay (ELISA) Quantitative assay of immunoglobulin G," *Immunochem 8*: 871-874 (1971).

Fertel R. and Weiss, B., *Methods in Enzymol*. vol. LV II, *Bioluminescence and Chemiluminescnece*, DeLuca, M.A. (Ed.) 94-106 (1978).

Hamaguchi et al., "Enzyme-Linked Sandwich Immunoassay of Macromolecular Antigens Using the Rabbit Antibody-Coupled Glass Rod as a Solid Phase," *Eur. J. Biochem.* 7: 459-467 (1976) and *FEBS Letters:* 69(1): 11-14 (1976).

Hofmann et al., "Iminobiotin Affinity Columns and Their Application to Retrieval of Streptavidin", *Proc. Natl. Acad. Sci. USA*, 77, No. 8, pp. 4666-4668 (1980).

Miranda, Q.R:, et al., "Solid-Phase Enzyme Immunoassay for Herpes Simplex Virus," *J. Infectious Disease 136*: S304-S310 (Oct., 1977).

Langer and Ward, Abstract 1153: A Rapid and Sensitive Immunological Method for *In Situ* Gene Mapping in *Journal of Supramolecular Structure and Cellular Biology*, (1981).

Langer and Ward, "A Rapid and Sensitive Immunological Method for In Situ Gene Mapping," in *Developmental Biology Using Purified Genes*, ed. D.D. Brown, Academic Press, pp. 647-658 (1981).

Mosback, K., et al., "immobilized Coenzymes," *Methods in Enzymology*, vol. XLIV: 859-887 (1976).

Nishimura et al. "Synthetic Nucleosides and Nucleotides: 5-Dimethylamino-2-oxidoisoquinolin-1 yl Diazomethane: A Novel Water Soluble Fluorescent Labelling Agent for Nucleotides," *Chem. Pharm. Bull.*, 28(6): 1695-1703 (1980).

Rosswell, D.F. and White E.H., "The Chemiluminescence of Luminol and Related Hydrazides" in *Methods in Enzymol.* vol. LV II, *Bioluminescence and Chemiluminescnece*, DeLuca, M.A. (Ed.) 409-423 (1978).

Schott, H., et al., "A Dihydroxyboryl-Substituted Methacrylic Polymer for the Column Chromatographic Separation of Mononucleotides, Oligonucleotides, and Transfer Ribonucleic Acid," *Biochemistry 12*: 932-937 (1973).

Rudkin and Stollar, "High Resolution Detection of DNA-RNA Hybrids *in situ* by Indirect Immunofluorescence," *Nature*, 265: 472-73 (1977).

Sodja and Davidson, "Gene Mapping and Gene Enrichment by the Avidin-Biotin Interaction: Use of Cytochrome-C as a Polyamine Bridge," *Nucl. Acids. Res*, 5, pp. 385-400 (1978).

Voller et al., "Enzyme immunoassays with special reference to ELISA techniques," *J. Clinical Pathology*, 31: 507-520 (1978).

Towbin H. et al., "Electrophoretic transfer of proteins from polyacrylamide gels to nitrocellulose sheets: Procedure and some applications," *Proc. Natl. Acad. Sci (USA)* 76: 4350-4354 (1979).

Weissback, A., and Poonian, M., "Nucleic Acids Attached to Solid Matrices," *Methods in Enzymology*, vol. XXXIV, Part B: 463-475 (1974).

Van Weemen and Schuurs, "Immunoassay Using Antigen-Enzyme Conjugates," *FEBS Letters 15*, No. 3: 232-236 (1971).

Mathews, J.C. and Cormier, M.J., "Rapid Microassay for the Calcium-Dependent Protein Modulator of Cyclic Nucleotide Phosphodiesterase," *Methods in Enzymol.* vol. LV II, *Bioluminescence and Chemiluminescnece*, DeLuca, M.A. (Ed.) 107-108 (1978).

"Diagnostic Immunology: Current and Future Trends," *Cap Conference*, Aspen, 1978, p. 67 and 80.

Voller et al., "A microplate method of enzyme-linked immunosorbent assay and its application to malaria," *Bull, W.H.O.*, 51: 209-211 (1974).

Szostak et al., "Hybridization with Synthetic Oligonucleotides," *Methods in Enzymol.* 68: 419-429 (1979).

So, et al., "Characterization of an *Escherichia coli* Plasmid Encoding for the Synthesis of Heat-Labile Toxin: Molecular Cloning of the Toxin Determinant", *Infection and Immunity*, 21: 405-11(1978).

Reiser et al., "Transfer of Small DNA Fragments from Polyacrylamide Gels to Diazobenzyloxymethyl-paper and Detection by Hybridization with DNA Probes," *Biochem. And Biophys. Res. Comm.*, 85, No. 3, pp. 1104-1112 (1978).

Mesulam, M. M. and Rosene, D.L., "Sensitivity in Horse-radish Peroxidase Neurohistochemistry: A Comparative Study of Nine Methods," *J. Histochem. Cytochem.* 27: No. 3, pp. 763-778 (1979).

Land, D.B. and Jackim, E., "A New Fluorescence-Yielding Substrate for Alkaline and Acid Phosphatase," *Analytical Biochemistry*, 16: 481-486 (1966).

Kochetkov, N.K. et al., *Organic Chemistry of Nucleic Acids, Part B*, Kochetkov, N.K., and Budovskii, E.I. (Eds.): 331-332 (1972).

Huang and Pagano, "Nucleic Acid Hybridization Technology and Detection of Proviral Genomes," *Methods in Virology.*, 6: 457-97 (1977).

Fertel R. and Weiss, B., "Measurement of the Activity of Cyclic Nucleotide Phosphodiesterases with Firefly Luciferin-Luciferase Coupled Assay Systems," *Methods in Enzymol.* vol. LVII, *Bioluminescence and Chemiluminescnece*, DeLuca, M.A. (Ed.) 94-96 (1978).

Dallas et al. "The Characterization of an *Escherichia coli* Plasmid Determinant That Encodes for the Production of a Heat-Labile Enterotoxin," *Plasmids of Medical Environmental and Commercial Importance*, K.N. Timmis and A. Puhler, editors, Elservier/North-Holland Biomedical Press (1979).

Hofmann et al., "Characterization of the Functional Groups of Bioten", *J. Biol. Chem.*, 141, 207-11 (1941).

*Elisa: In The Clinical Microbiology Laboratory*, ed. T. G. Wreghitt and P. Morgan-Capner, Chapter 1, p. 9, 1990.

Dallas and Falkow, "Molecular and Genetic Analysis of a DNA sequence Encoding for Enterotoxin Synthesis in *Escherichia coli,"* *Thriteenth Joint Conference on Cholera*, The U.S.—Japan Cooperative Medical Science Program (1977).

Stuart, W.D., et al., "Location of the 18/28S ribosomal RNA genes in two Hawaiian *Drosophila* species by monoclonal immunological identification of RNA-DNA hybrids *in situ*," Proc. Natl. Acad. Sci. USA 78:3751-3754 (1981).

Haugen et al., Monoclonal antibody to aflatoxin B1-modified DNA detected by enzyme immunoassay, PNAS, 78, pp. 4124-4127 (1981).

Vogelstein, B. and Gillespie, D., Preparative and Analytical Purification of DNA From Agarosa, Proc. Natl. Acad. Sci. USA vol. 76, No. 2, pp. 615-619, Feb. 1979.

Munns and Liszewski, "Antibodies specific for Modified Nucleosides et al.," Progr. Nucl. Acid Res. & Molec. Bio., Academic Press, Inc., vol. 24, pp. 109-165 (1980).

Nagata et al., "Quantification of picogram levels of specific DNA immobilized in microtiter wells," FEBS, 183, pp. 379-382 (Apr. 1985).

Sedlacek, H. et al., A New Method for Fluorescence Immunoassay Using Plane Surface Solid Phases (FIAPS), J. Immun. Methods, 26, (1979) 11-24.

Van Der Laken et al., "Measurement of O6-ethyldeoxyguanosine and N-(deoxyguanosin-8-yl)-N-acetyl-2-aminofluorene in DNA et al.," Carcinogenesis, 3, 569-572 (1982).

Joseph Gall and Mary Lou Perdue, Formation and Detection of RNA-DNA Hybrid Molecules in Cytological Preparations, Genetics, 63: 378-383, Mar. 1969.

Buongiorno-Nardelli, M. and Amaldi, F., Autoradiographic Detection of Molecular Hybrids Between rRNA and DNA in Tissue Sections, Nature, vol. 225, Mar. 7, 1970.

Ueda R. et al., Serological Analysis of Cell Surface Antigens of Null Cell Acute Lymphocytic Leukemia by et al., Proc. Natl. Acad. Sci. USA, vol. 79, pp. 4386-4390, Jul. 1982.

Method in Nucleic Acid Research, "DNA-DNA Hybridization", Kyoritsu Shuppan Co., Ltd., 1973, pp. 60-67 and 242.

English Translation for Method in Nucleic Acid Research, "DNA-DNA Hybridization", Kyoritsu Shuppan Co., Ltd., 1973, pp. 60-67 and 242.

Dictionary of Biochemistry, Tokyo Kagaku Doujin, 1984, pp. 727, 507, 450 and one other page.

English Translation for Dictionary of Biochemistry, Tokyo Kagaku Doujin, 1984, pp. 727, 507, 450 and one other page.

Mage M.G. et al, *Journal of Immunological Methods* 15:47-56 (1977).

Wysocki L.J. and Sato, V.L., *Proc.Natl.Acad.Sci (USA)* 75(6):2844-2848 (Jun. 1978).

Landreth K.S. et al., *roc.Natl.Acad.Sci (USA)* 79:2370-2374 (1982).

Bunemann H. et al., *Nucleic Acids Research* 10(22):7163-7180 (1982).

Bunemann H., *Nucleic Acids Research* 10(22):7181-7196 (1982).

Beltz G.A. et al., *Methods in Enzymology* 100:266-285 (1983).

Kafatos F.C et al., *Nucleic Acids Research* 7(6): 1541-1552 (1979).

Masiakowski P. et al., *Nucleic Acids Research* 10(24):7895-7903 (1982).

Sim G.K. et al., *Cell* 18:1303-1316 (1979).

Frank R. et al., *Nucleic Acids Research* 11(13):4365-4377 (1983).

Calva E. et al., *The Journal of Biological Chemistry* 255(22):11011-11016 (1980).

Wengler G. et al., *Virology* 78:124-134 (1977).

Coffin J.M. et al., *Cell* 13:761-773 (1978).

Manning J.E. et al., *Chromosoma (Berl.)* 53:107-117 (1975).

Manning J. et al., *Biochemistry* 16(7): 1364-1370 (1977).

Maxam, A.M. and Gilbert, W., *Methods in Enzymology* 65:499-560 (1980).

Sanger, F. et al., *Proc. Natl. Acad. Sci (USA)* 74(12):5463-5467 (1977).

Amit B. et al., *Journal of Organic Chemistry* 39(2): 192-196 (1974).

Amit B. et al., *Israel Journal of Chemistry* 12(1-2): 103-113 (1974).

Barltrop J.A. et al., *Chemical Communications* 22:822-823 (1966).

Flanders D.C. and Smith, H.I., *Applied Physics Letters* 31(7):426-428 (1977).

Krile T.F. et al., *Applied Optics* 18(1):52-56 (1979).

Ohtsuka E. et al., *Nucleic Acids Research* 1(10):1351-1357 (1974).

Patchornik A. and Amit B., *Journal of the American Chemical Society* 92:6333-6335 (1970).

Pillai V.N.R., *Synthesis* (International Journal of Methods in Synthetic Organic Chemistry Chemistry), Schill, G. et al., eds., Georg Thieme Verlag publishers, Stuttgart and New York, pp. 1-26, published 1980.

Zehavi U. et al., *Journal of Organic Chemistry* 37(14):2281-2285 (1972).

Seed B., *Nucleic Acids Research* 10(5):1799-1810 (1982).

* cited by examiner

SYSTEM, ARRAY AND NON-POROUS SOLID SUPPORT COMPRISING FIXED OR IMMOBILIZED NUCLEIC ACIDS

CROSS-REFERENCE TO OTHER RELATED APPLICATIONS

This is a continuation application of U.S. Patent Application Ser. No. 07/967,646, filed on Oct. 28, 1992, now abandoned, which application is a continuation application of U.S. Patent Application Ser. No. 07/607,347, filed on Oct. 30, 1990, also abandoned. Ser. No. 07/607,347 is a continuation of U.S. Patent Application Ser. No. 07/385,986, filed on Jul. 20, 1989, now U.S. Pat. No. 4,994,373 issued on Feb. 19, 1991. Ser. No. 07/385,986 is a continuation of U.S. Patent Application Ser. No. 06/732,374, filed on May 9, 1985, also abandoned, which application is a continuation-in-part of U.S. Patent Application Ser. No. 06/461,469, filed on Jan. 27, 1983, also abandoned.

TECHNICAL FIELD OF INVENTION

The present invention relates generally to the detection of genetic material by polynucleotide probes. More specifically, it relates to a method for quantifiably detecting a targeted polynucleotide sequence in a sample of biological and/or nonbiological material employing a probe capable of generating a soluble signal. The method and products disclosed herein in accordance with the invention are expected to be adaptable for use in many laboratory, industrial, and medical applications wherein quantifiable and efficient detection of genetic material is desired.

BACKGROUND OF THE INVENTION

In the description, the following terms are employed:

Analyte—A substance or substances, either alone or in admixtures, whose presence is to be detected and, if desired, quantitated. The analyte may be a DNA or RNA molecule of small or high molecular weight, a molecular complex including those molecules, or a biological system containing nucleic acids, such as a virus, a cell, or group of cells. Among the common analytes are nucleic acids (DNA and RNA) or segments thereof, oligonucleotides, either single- or double-stranded, viruses, bacteria, cells in culture, and the like. Bacteria, either whole or fragments thereof, including both gram positive and gram negative bacteria, fungi, algae, and other microorganisms are also analytes, as well as animal (e.g., mammalian) and plant cells and tissues.

Probe—A labelled polynucleotide or oligonucleotide sequence which is complementary to a polynucleotide or oligonucleotide sequence of a particular analyte and which hybridizes to said analyte sequence.

Label—That moiety attached to a polynucleotide or oligonucleotide sequence which comprises a signalling moiety capable of generating a signal for detection of the hybridized probe and analyte. The label may consist only of a signalling moiety, e.g., an enzyme attached directly to the sequence. Alternatively, the label may be a combination of a covalently attached bridging moiety and signalling moiety or a combination of a non-covalently bound bridging moiety and signalling moiety which gives rise to a signal which is detectable, and in some cases quantifiable.

Bridging Moiety—That portion of a label which on covalent attachment or non-covalent binding to a polynucleotide or oligonucleotide sequence acts as a link or a bridge between that sequence and a signalling moiety.

Signalling Moiety—That portion of a label which on covalent attachment or non-covalent binding to a polynucleotide or oligonucleotide sequence or to a bridging moiety attached or bound to that sequence provides a signal for detection of the label.

Signal—That characteristic of a label or signalling moiety that permits it to be detected from sequences that do not carry the label or signalling moiety.

The analysis and detection of minute quantities of substances in biological and non-biological samples has become a routine practice in clinical, diagnostic and analytical laboratories. These detection techniques can be divided into two major classes: (1) those based on ligand-receptor interactions (e.g., immunoassay-based techniques), and (2) those based on nucleic acid hybridization (polynucleotide sequence-based techniques).

Immunoassay-based techniques are characterized by a sequence of steps comprising the non-covalent binding of an antibody and antigen complementary to it. See, for example, T. Chard, *An Introduction To Radioimmunoassay And Related Techniques* (1978).

Polynucleotide sequence-based detection techniques are characterized by a sequence of steps comprising the non-covalent binding of a labelled polynucleotide sequence or probe to a complementary sequence of the analyte under hybridization conditions in accordance with the Watson-Crick base pairing of adenine (A) and thymine (T), and guanine (G) and cytosine (C), and the detection of that hybridization. [M. Grunstein and D. S. Hogness, "Colony Hybridization: A Method For The Isolation Of Cloned DNAs That Contain A Specific Gene", *Proc. Natl. Acad. Sci. USA*, 72, pp. 3961–65 (1975)]. Such polynucleotide detection techniques can involve a fixed analyte [see, e.g., U.S. Pat. No. 4,358,535 to Falkow et al], or can involve detection of an analyte in solution [see U.K. patent application 2,019,408 A].

The primary recognition event of polynucleotide sequence-based detection techniques is the non-covalent binding of a probe to a complementary sequence of an analyte, brought about by a precise molecular alignment and interaction of complementary nucleotides of the probe and analyte. This binding event is energetically favored by the release of non-covalent bonding free energy, e.g., hydrogen bonding, stacking free energy and the like.

In addition to the primary recognition event, it is also necessary to detect when binding takes place between the labelled polynucleotide sequence and the complementary sequence of the analyte. This detection is effected through a signalling step or event. A signalling step or event allows detection in some quantitative or qualitative manner, e.g., a human or instrument detection system, of the occurrence of the primary recognition event.

The primary recognition event and the signalling event of polynucleotide sequence based detection techniques may be coupled either directly or indirectly, proportionately or inversely proportionately. Thus, in such systems as nucleic acid hybridizations with sufficient quantities of radiolabeled probes, the amount of radio-activity is usually directly proportional to the amount of analyte present. Inversely proportional techniques include, for example, competitive immuno-assays, wherein the amount of detected signal decreases with the greater amount of analyte that is present in the sample.

Amplification techniques are also employed for enhancing detection wherein the signalling event is related to the primary recognition event in a ratio greater than 1:1. For example, the signalling component of the assay may be present in a ratio of 10:1 to each recognition component, thereby providing a 10-fold increase in sensitivity.

A wide variety of signalling events may be employed to detect the occurrence of the primary recognition event. The signalling event chosen depends on the particular signal that characterizes the label or signalling moiety of the polynucleotide sequence employed in the primary recognition event. Although the label may only consist of a signalling moiety, which may be detectable, it is more usual for the label to comprise a combination of a bridging moiety covalently or non-covalently bound to the polynucleotide sequence and a signalling moiety that is itself detectable or that becomes detectable after further modification.

The combination of bridging moiety and signalling moiety, described above, may be constructed before attachment or binding to the sequence, or it may be sequentially attached or bound to the sequence. For example, the bridging moiety may be first bound or attached to the sequence and then the signalling moiety combined with that bridging moiety. In addition, several bridging moieties and/or signalling moieties may be employed together in any one combination of bridging moiety and signalling moiety.

Covalent attachment of a signalling moiety or bridging moiety/signalling moiety combination to a sequence is exemplified by the chemical modification of the sequence with labels comprising radioactive moieties, fluorescent moieties or other moieties that themselves provide signals to available detection means or the chemical modification of the sequence with at least one combination of bridging moiety and signalling moiety to provide that signal.

Non-covalent binding of a signalling moiety or bridging moiety/signalling moiety to a sequence involve the non-covalent binding to the sequence of a signalling moiety that itself can be detected by appropriate means, i.e., or enzyme, or the non-covalent binding to the sequence of a bridging moiety/signalling moiety to provide a signal that may be detected by one of those means. For example, the label of the polynucleotide sequence may be a bridging moiety non-covalently bound to an antibody, a fluorescent moiety or another moiety which is detectable by appropriate means. Alternatively, the bridging moiety could be a lectin, to which is bound another moiety that is detectable by appropriate means.

There are a wide variety of signalling moieties and bridging moieties that may be employed in labels for covalent attachment or non-covalent binding to polynucleotide sequences useful as probes in analyte detection systems. They include both a wide variety of radioactive and non-radioactive signalling moieties and a wide variety of non-radioactive bridging moieties. All that is required is that the signalling moiety provide a signal that may be detected by appropriate means and that the bridging moiety, if any, be characterized by the ability to attach covalently or to bind non-covalently to the sequence and also the ability to combine with a signalling moiety.

Radioactive signalling moieties and combinations of various bridging moieties and radioactive signalling moieties are characterized by one or more radioisotopes such as $^{32}P$, $^{131}I$, $^{14}C$, $^{3}H$, $^{60}Co$, $^{59}Ni$, $^{63}Ni$ and the like. Preferably, the isotope employed emits β or γ radiation and has a long half life. Detection of the radioactive signal is then, most usually, accomplished by means of a radioactivity detector, such as exposure to a film.

The disadvantages of employing a radioactive signalling moiety on a probe for use in the identification of analytes are well known to those skilled in the art and include the precautions and hazards involved in handling radioactive material, the short life span of such material and the correlatively large expenses involved in use of radioactive materials.

Non-radioactive signalling moieties and combinations of bridging moieties and non-radioactive signalling moieties are being increasingly used both in research and clinical settings. Because these signalling and bridging moieties do not involve radioactivity, the techniques and labelled probes using them are safer, cleaner, generally more stable when stored, and consequently cheaper to use. Detection sensitivities of the non-radioactive signalling moieties also are as high or higher than radio-labelling techniques.

Among the presently preferred non-radioactive signalling moieties or combinations of bridging/signalling moieties useful as non-radioactive labels are those based on the biotin/avidin binding system. [P. R. Langer et al., "Enzymatic Synthesis Of Biotin-Labeled Polynucleotides: Novel Nucleic Acid Affinity Probes", *Proc. Natl. Acad. Sci. USA*, 78, pp. 6633–37 (1981); J. Stavrianopoulos et al., "Glycosylated DNA Probes For Hybridization/Dection Of Homologous Sequences", presented at the Third Annual Congress For Recombinant DNA Research (1983); R. H. Singer and D. C. Ward, "Actin Gene Expression Visualized In Chicken Muscle Tissue Culture By Using In Situ Hybridization With A Biotinated Nucleotide Analog", *Proc. Natl. Acad. Sci. USA*, 79, pp. 7331–35 (1982)]. For a review of non-radioactive signalling and bridging/signalling systems, both biotin/avidin and otherwise, see D. C. Ward et al., "Modified Nucleotides And Methods Of Preparing And Using Same", European Patent application No. 63879.

The above-referenced U.S. Patent Application Ser. No. 06/255,223 was abandoned in favor of continuation application, U.S. Patent Application Ser. No. 06/496,915, filed on May 23, 1983, now U.S. Pat. No. 4,711,955. A related divisional application of the aforementioned Ser. No. 06/496,915 was filed (on Dec. 8, 1987) as U.S. Patent Application Ser. No. 07/130,070 and issued on Jul. 12, 1994 as U.S. Pat. No. 5,328,824. Two related continuation applications of the aforementioned Ser. No. 07/130,070 were filed on Feb. 26, 1992 (as Ser. No. 07/841,910) and on May 20, 1992 as (Ser. No. 07/886,660). The aforementioned applications, Ser. No. 07/886,660 and Ser. No. 07/841,910, issued as U.S. Pat. Nos. 5,449,767 and 5,476,928 on Sep. 12, 1995 and Dec. 19, 1995, respectively. The above-referenced U.S. Patent Application Ser. No. 06/391,440, filed on Jun. 23, 1982, was abandoned in favor of U.S. Patent Application Ser. No. 07/140,980, filed on Jan. 5, 1988, the latter now abandoned. Two divisional applications of the aforementioned Ser. No. 07/140,980, U.S. Patent Applications Ser. Nos. 07/532,704 (filed on Jun. 4, 1990 for "Base Moiety Labeled Detectable Nucleotide") and 07/567,039 (filed on Aug. 13, 1990 for "Saccharide Specific Binding System Labeled Nucleotides") issued as U.S. Pat. Nos. 5,241,060 (Aug. 31, 1993) and 5,260,433 (Nov. 9, 1993), respectively. The disclosures of the above-identified *PNAS* article (P. R. Langer et al., "Enzymatic Synthesis of Biotin-Labeled Polynucleotides: Novel Nucleic Acid Affinity Probes," *Proc. Natl. Acad. Sci.(USA)* 78:6633–6637 (1981) and U.S. Pat. Nos. 4,711,955, 5,328,824, 5,449,767, 5,476,928, 5,241,060, 5,260,433, and 4,358,535 are herein incorporated and made part of this disclosure.

Generally, the signalling moieties employed in both radioactive and non-radioactive detection techniques involve the use of complex methods for determining the signalling event, and/or supply only an unquantitable positive or negative response. For example, radioactive isotopes must be read by a radioactivity counter; while signalling moieties forming insoluble "signals", i.e., precipitates, certain fluorescers, and the like [see, e.g., David et al., U.S. Pat. No. 4,376,100] only provide detection not quantitation of the analyte present in the tested sample.

One step toward facilitating rapid and efficient quantitation as well as detection of the hybridization event was the work of Heller et al. in European Patent Applications No. 70685 and 70687 which describe the use of a signalling moiety which produces a soluble signal for measurable detection by a spectrophotometer. These European patent applications disclose the use of two different probes complementary to different portions of a gene sequence, with each probe being labelled at the end which will abut the other probe upon hybridization. The first probe is labelled with a chemiluminescent complex that emits lights of a specific wavelength. The second probe is labelled with a molecule that emits light of a different wavelength measurable by spectrophotometry when excited by the proximity of the first signalling moiety. However, this technique is performed in solution and can generate false positive results in the absence of the analyte if the two probes happen to approach too closely in solution and react with each other.

Similarly, U.K. Patent Application 2,019,408A, published Oct. 31, 1979, discloses a method for detecting nucleic acid sequences in solution by employing an enzyme-labelled RNA or DNA probe which, upon contact with a chromogen substrate, provides an optically readable signal. The analytes may be separated from contaminants prior to hybridization with the probe, or, alternatively, the hybrid probe-analyte may be removed from solution by conventional means, i.e., centrifugation, molecular weight exclusion, and the like. Like Heller's technique, this method is performed in solution.

There remains therefore a need in the art for a reliable, simple and quantifiable technique for the detection of analytes of interest in biological and non-biological samples.

SUMMARY OF THE INVENTION

The invention provides a solution for the disadvantages of presently available methods of detecting analytes by a novel combination of hybridization and immunological techniques. In the present invention, chemically labelled polynucleotide or oligonucleotide probes are employed to detect analytes by having the capacity to generate a reliable, easily quantifiable soluble signal.

Analytes to be detected by the detection processes of this invention may be present in any biological or non-biological sample, such as clinical samples, for example, blood urine, feces, saliva, pus, semen, serum, other tissue samples, fermentation broths, culture media, and the like. If necessary, the analyte may be pre-extracted or purified by known methods to concentrate its nucleic acids. Such nucleic acid concentration procedures include, for example, phenol extraction, treatment with chloroform-isoamyl alcohol or chloroform-octanol, column chromatography (e.g., Sephadex, hydroxyl apatite), and CsCl equilibrium centrifugation. The analyte, separated from contaminating materials, if present, is according to the present invention, fixed in hybridizable form to a solid support.

Analytes in a biological sample are preferably denatured into single-stranded form, and then directly fixed to a suitable solid support. Alternatively, the analyte may be directly fixed to the support in double-stranded form, and then denatured. The present invention also encompasses indirect fixation of the analyte, such as in in situ techniques where the cell is fixed to the support and sandwich hybridization techniques where the analyte is hybridized to a polynucleotide sequence that is fixed to the solid support. It is preferred that the solid support to which the analyte is fixed be non-porous and transparent, such as glass, or alternatively, plastic, polystyrene, polyethylene, dextran, polypropylene and the like. Conventional porous materials, e.g., nitrocellulose filters, although less desirable for practice of the method of the present invention, may also be employed as a support.

It is also highly desirable that the analyte be easily fixed to the solid support. The capability to easily fix the analyte to a transparent substrate would permit rapid testing of numerous samples by the detection techniques described herein.

Chemically-labeled probes are then brought into contact with the fixed single-stranded analytes under hybridizing conditions. The probe is characterized by having covalently attached to it a chemical label which consists of a signalling moiety capable of generating a soluble signal. Desirably, the polynucleotide or oligonucleotide probe provides sufficient number of nucleotides in its sequence, e.g., at least about 25, to allow stable hybridization with the complementary nucleotides of the analyte. The hybridization of the probe to the single-stranded analyte with the resulting formation of a double-stranded or duplex hybrid is then detectable by means of the signalling moiety of the chemical label which is attached to the probe portion of the resulting hybrid. Generation of the soluble signal provides simple and rapid visual detection of the presence of the analyte and also provides a quantifiable report of the relative amount of analyte present, as measured by a spectrophotometer or the like.

The method of the present invention involving the colorimetric or photometric determination of the hybridized probes employs as the signalling moiety reagents which are capable of generating a soluble signal, e.g., a color change in a substrate in solution. Preferable components of the signalling moiety include enzymes, chelating agents and co-enzymes, which are able to generate colored or fluorescent soluble signals. Specifically, certain chromogens upon contact with certain enzymes are utilizable in the method of the present invention. The following Table I lists exemplary components for the signalling moiety of the present invention. Each chromogen listed is reactive with the corresponding enzyme to produce a soluble signal which reports the presence of the chemically-labeled probe analyte hybrid. The superscript notation (*) indicates that the chromogen fluoresces, rather than produces a color change.

TABLE I

| ENZYME | CHROMOGEN |
| --- | --- |
| alkaline phosphatase or acid phosphatase | *4-Methylumbelliferyl phosphate *bis (4-Methylumbelliferyl phosphate 3-0-methylfluorescein. *Flavone-3-diphosphate triammonium salt p-nitrophenyl phosphate 2Na. |
| peroxidase | *Tyramine hydrochloride *3-(p-hydroxyphenyl) Propionic acid *p-Hydroxyphenethyl alcohol 2,2'-Azino-Di-3-Ethylbenzthiazoline |

TABLE I-continued

| ENZYME | CHROMOGEN |
|---|---|
|  | sulfonic acid (ABTS) |
|  | ortho-phenylenediamine 2HCl |
|  | 0-dianisidine |
|  | *5-aminosalicylic acid |
|  | p-cresol |
|  | 3,3'-dimethyloxybenzidine |
|  | 3-methyl-2-benzothiazoline hydrazone |
|  | tetramethyl benzidine |
| β-D-galactosidase | 0-nitrophenyl β-D-galactopyranoside |
|  | 4-methylumbelliferyl-β-D-galactoside |
| glucose-oxidase | ABTS |

As another aspect of the present invention, the signalling moiety may be attached to the probe through the formation of a bridging entity or complex. Likely candidates for such a bridging entity would include a biotin-avidin bridge, a biotin-streptavidin bridge, or a sugar-lectin bridge.

Once the fixed probe-analyte hybrid is formed, the method may further involve washing to separate any non-hybridized probes from the area of the support. The signalling moiety may also be attached to the probe through the bridging moiety after the washing step to preserve the materials employed. Thereafter, another washing step may be employed to separate free signalling moieties from those attached to the probe through the bridging moiety.

Broadly, the invention provides hybridization techniques which provide the same benefits as enzyme linked immunosorbent assay techniques, i.e, the qualitative and quantitative determination of hybrid formation through a soluble signal. Various techniques, depending upon the chemical label and signalling moiety of the probe, may be employed to detect the formation of the probe-analyte hybrid. It is preferred, however, to employ spectrophotometric techniques and/or colorimetric techniques for the determination of the hybrid. These techniques permit not only a prompt visual manifestation of the soluble signal generated by the signalling moiety on the double-stranded hybrid, but also permit the quantitative determination thereof, i.e., by the enzymatic generation of a soluble signal that can be quantitatively measured.

Yet another aspect of the method of the present invention involves generating the soluble signal from the probe-analyte hybrid in a device capable of transmitting light therethrough for the detection of the signal by spectrophotometric techniques. Examples of devices useful in the spectrophotometric analysis of the signal include conventional apparatus employed in diagnostic laboratories, i.e., plastic or glass wells, tubes, cuvettes or arrangements of wells, tubes or cuvettes. It may also be desirable for both the solid support to which the analyte is fixed and the device to be composed of the same material, or for the device to function as the support in addition to facilitating spectrophotometric detection.

A further aspect of the present invention provides products useful in the disclosed method for detection of a polynucleotide sequence. Among these products is a device containing a portion for retaining a fluid. Such portion contains an immobilized polynucleotide sequence hybridized to a polynucleotide or oligonucleotide probe. The probe, as described above, has covalently attached thereto a chemical label including a signalling moiety capable of generating a soluble signal. Also part of the device is a soluble signal, preferably a colored or fluorescent product, generatable by means of the signalling moiety. The portion of the device for containing the fluid is desirably a well, a tube, or a cuvette. A related product of the invention is an apparatus comprising a plurality of such devices for containing a fluid, in which at least one such device contains the above-described immobilized polynucleotide sequence, polynucleotide or oligonucleotide probe, signalling moiety, and soluble signal. Additionally the present invention provides for the novel product of a non-porous solid support to which a polynucleotide is directly fixed in hybridizable form. Such a fixed sequence may be hybridized to another polynucleotide sequence having covalently attached thereto a chemical label including a signalling moiety capable of generating a soluble signal. As indicated above, the support is preferably transparent or translucent. Such products could be advantageously employed in diagnostic kits and the like.

Other aspects and advantages of the present invention will be readily apparent upon consideration of the following detailed description of the preferred embodiments thereof.

DETAILED DESCRIPTION

The following examples are illustrative of preferred embodiments of the method of the present invention. Specifically referred to therein are methods for fixing the analyte to a non-porous solid support, as well as illustrations of the use of soluble signals in polynucleotide probes as discussed above.

EXAMPLE 1

For purposes of the present invention, an analyte is immobilized on a solid support, preferably a non-porous translucent or transparent support. To effect easy fixing of a denatured single-stranded DNA sequence to a glass support, an exemplary "fixing" procedure may involve pretreating the glass by heating or boiling for a sufficient period of time in the presence of dilute aqueous nitric acid. Approximately forty-five minutes in 5% dilute acid should be adequate to leach boron residues from a borosilicate glass surface. The treated glass is then washed or rinsed, preferably with distilled water, and dried at a temperature of about 115° C., for about 24 hours. A 10 percent solution of gamma-aminopropyltriethoxysilane, which may be prepared by dissolving the above-identified silane in distilled water followed by addition of 6N hydrochloric acid to a pH of about 3.45, will then be applied to the glass surface. The glass surface is then incubated in contact with the above-identified silane solution for about 2–3 hours at a temperature of about 45° C. The glass surface is then washed with an equal volume of water and dried overnight at a temperature of about 100° C. The resulting treated glass surface will now have available alkylamine thereon suitable for immobilizing or fixing any negatively charged polyelectrolytes applied thereto. [See Weetal, H. H. and Filbert, A. M., "Porous Glass for Affinity Chromatography Applications", *Methods in Enzymology*, Vol. XXXIV, Affinity Techniques Enzyme Purification: Part B. pp. 59–72, W. B. Jakoby and M. Wilchek, eds.]

Such treated glass could then be employed in the method of the invention. For example, glass plates provided with an array of depressions or wells would have samples of the various denatured analytes deposited therein, the single-stranded analytes being fixed to the surfaces of the wells. Thereupon, polynucleotide probes provided with a chemical label may be deposited in each of the wells for hybridization to any complementary single-stranded analyte therein. After washing to remove any non-hybridized probe, the presence of any hybrid probe-analyte is detectable One then detection - - - technique as described herein involves the addition of an enzyme-linked antibody or other suitable bridging entity of the label for attachment to the probe. Subsequently a suitable substrate is added to elicit the soluble signal, e.g., a color change or chemical reaction, which is then measured colorimetrically or photometrically.

This invention also provides an apparatus comprising a plurality of means for containing a fluid, wherein at least one of the means comprises (i) an immobilized polynucleotide sequence hybridized to a polynucleotide or oligonucleotide probe, the probe having covalently attached thereto, a chemical label comprising a signalling moiety capable of forming a soluble signal, and (ii) a soluble signal generated by means of the signalling moiety.

Also provided by this invention is a non-porous solid support having directly fixed thereto a polynucleotide sequence in hybridizable form. Such a support is characterized in that the polynucleotide sequence is hybridized to a polynucleotide or oligonucleotide probe, the probe having covalently attached thereto a chemical label comprising a signalling moiety capable of generating a soluble signal. Such a support is also characterized in that the support is a transparent or translucent support.

EXAMPLE 2

A glass surface treated as described in Example 1 can be employed in the method of the present invention, wherein glucosylated DNA is employed as the labelled probe, and the signalling moiety comprises the combination of acid phosphatase and its substrate paranitrophenylphosphate.

In this procedure, glucosylated bacteriophage $T_4$ DNA, isolated from *E. coli* CR63 cultures infected with phage $T_4$ AM82 [44$^-$62$^-$] and purified to be free of chromosomal DNA, or non-glucosylated, highly purified calf thymus DNA is delivered in 100 μl portions to treated glass tubes in triplicate set. After 15–30 minutes at room temperature, the solution is removed and the tubes rinsed generously with PBS·Mg$^{++}$ buffer [100 mM Na—K—PO$_4$, pH 6.5, 150 mM NaCl and 10 mM MgCl$_2$].

One set of tubes is checked for the presence of DNA by staining with ethidium bromide [100 μl of 1 mg/ml solution, 30 minutes in the dark, at room temperature]. The staining solution is removed and the tubes rinsed and checked by UV light. Both glucosylated labelled and unlabelled DNA "probe" bound to the activated glass surface by the observed red fluorescence characteristic of ethidium bromide.

To another set of tubes is delivered fluorescein-labelled ConA [100 μl of 0.1 mg/ml in PBS·Mg$^{++}$ buffer]. The Concanavalin A [ConA] is obtained and solubilized in 2.0 M NaCl at a concentration of 50 mg/ml, and fluorescein-labelled by reacting ConA with fluorescein isothiocyanate at an FITC to protein molar ratio of 3 to 1 in 0.1 M sodium borate solution at a pH of 9.2 and at a temperature of 37° C. for 60 minutes. Any unreacted FITC is removed by gel filtration on Sephadex G-50. After 60 minutes at room temperature, the solution is removed and the tubes rinsed and checked under UV light. ConA bound only to glucosylated DNA in tubes containing $T_4$ DNA.

To the third set of tubes is delivered 100 μl of unlabeled ConA in PBS·Mg$^{++}$ buffer. After 60 minutes at room temperature, the tubes are rinsed free of ConA with 0.2 M Imidazole buffer pH 6.5.

Acid phosphatase is then added [0.005 units in 100 μl at 0.2 percent phosphatase-free BSA] and the tubes are incubated at room temperature for 30 minutes. After rinsing with 0.15 M NaCl to remove any unbound enzyme, 0.1 mM paranitrophenylphosphate in 0.2 M imidazole at pH 6.5 is added and incubation continued for 60 minutes at 37° C. The enzyme reaction is terminated by adding 1.0 ml of 0.5 percent sodium bicarbonate and absorbance is determined at $^A$300.

The resulting observed test results indicate that acid phosphatase, one component of the signalling moiety gives a positive visible color reaction, upon reaction with its chromogen, only in tubes containing "probe" $T_4$ DNA and bridging moiety, ConA, but is washed off from the tubes which contain only ConA or ConA and calf thymus DNA.

EXAMPLE 3

In an example of the method of the present invention, phage lambda DNA was employed as the analyte, glucosylated DNA as the labelled probe, ConA as the bridging entity and alkaline phosphatase with paranitrophenylphosphate as the signalling moiety. Bacteriophage lambda, obtained by heat induction of *E. coli* stain W3350 lysogenic for $\gamma C_1$ 857 phage, was employed for the preparation of phage lambda DNA. In these tests, the analyte, phage lambda DNA, was immobilized on an activated glass surface according to the following procedure. After rinsing with buffer, glass tubes were coated with 100 μl of coating solution [50 percent formamide, 5X SSC, 100 μg salmon sperm DNA 0.2 percent polyvinyl pyrrolidone, 0.1 percent Triton X-100, 0.2 percent BSA and 0.05 percent SDS] at 42° C. for 90–120 minutes. The coating solution was removed and the surface was covered with 100 μl of coating solution containing phage lambda DNA.

Phage lamba DNA employed as the probe is nick translated with maltose-triose dUTP to introduce glucosyl residues into the DNA. The glucosylated minutes and rapidly cooled in ice bath immediately before use. The tubes were then incubated with probe at 42° C. for 24 hours. The solution was removed and tubes were rinsed with PBS·Mg$^{++}$ buffer. As described above in example 2, ConA is added to the tubes in PBS·Mg buffer. After 60 minutes at room temperature the tubes are rinsed with 0.2 M Imidazole buffer.

Also as described in Example 2, the signalling moiety components, acid phosphatase and paranitrophenyl phosphate, are sequentially introduced into the tubes, to generate the detectable soluble signal. In these tests, the glucosyl moiety of the DNA probe is one bridging moiety of the chemical label, and reacts with and is strongly attracted to the second bridging moiety, ConA. The results indicated that acid phosphatase was not washed off from the tubes which contained glucosylated probe, whereas tubes containing non-labelled probe did not show any enzyme activity.

EXAMPLE 4

As in the above example employing a glucosylated DNA as the labelled probe, wherein the glucosyl moiety serves as part of the chemical label, comparable results may also be achieved by employing a biotin-labeled DNA probe. When biotin is employed as a bridging moiety of the chemical label of the DNA probe, the presence of the biotin-labeled DNA probe would be elicited or detected by means of an avidin or streptavidin-linked enzyme, since avidin is strongly reactive with or strongly bonds to biotin.

For example, a biotin-labeled DNA probe would readily be detected by an enzyme complex of the character avidin-biotin-alkaline phosphatase. More specifically, the presence of the biotin-labeled DNA probe would readily be detected by contacting the hybrid containing the biotin-labeled probe with the enzyme complex avidin-biotin-alkaline phosphatase, and bringing the resulting probe and avidin-biotin-alkaline phosphatase complex into contact with a suitable substrate which, upon contact with the enzyme, would produce a soluble signal that would be readily noticed or be capable of being determined, both qualitatively and quantitatively, by photometric and/or colorimetric means. If desired, instead of an avidin-biotin-enzyme complex, there could be used an antibody to biotin for attachment to the biotin moiety of the biotin-labeled DNA probe, followed by a complex comprising anti-antibody-enzyme in the manner described above.

EXAMPLE 5

The advantages of this invention are also obtainable when the probe is immobilized on a non-porous plastic surface. When a plastic surface is employed, it is sometimes desirable to increase the effectiveness or uniformity of the fixation by pretreating the plastic surface.

Because polystyrene from various batches or sources exhibits different binding capacities, the adherence or fixing of DNA to a polystyrene surface is improved by treating the surface with an amino-substituted hydrophobic polymer or material. Previous experiments demonstrated that addition of duodecadiamine (DDA) to polystyrene resulted in an uniform binding coefficient of polystyrene plates of different batches. Another technique for improving the fixing or uniformity of the plastic surface for fixing DNA involves treatment of the surface with polylysine (PPL).

In tests involving the fixing of DNA to a plastic surface, biotinylated DNA (b-DNA) was denatured and aliquoted into Dynatech, Immulon II™ removable wells. Samples were allowed to dry onto the plastic surface at 37° C. The amount of bound b-DNA was determined by sequential addition of goat anti-biotin antibody and rabbit anti-goat antibody complexed to the signalling moiety, alkaline phosphatase, followed by development with p-nitrophenyl phosphate in diethanolamine buffer, pH 9.6. Enzymatic activity was monitored at 405 nm utilizing the automatic Dynatech Micro ELISA Scanner. This procedure enables quantitation of the amount of bound DNA and therefore the degree of biotinylation. To increase the sensitivity of detection, a fluorogenic substrate such as 4-methylumbelliferyl-phosphate, or its analogues, with companion enzymes, may be used.

In a further example of the method, denatured adenovirus 2 DNA, the analyte, was bound to polystyrene plates as described above. After blocking with Denhardt's formamide blocking buffer, several biotinylated probes, b-adeno-2-DNA and lambda DNA were hybridized to the immobilized DNA. To one set of immobilized DNA, no probe was added. The extent of hybridization was determined by means of the antibody-enzyme reaction as described above. It was observed that only the homologous adeno-2 probe hybridized. This technique demonstrated that in vitro hybridization under these conditions is specific and can be monitored quantitatively by the method of the present invention.

Other methods for enabling fixation of single-stranded analyte to a solid support for use in the method of the present invention include the following.

EXAMPLE 6

In further tests, radioactively-labeled DNA was prepared by nick translation with [$^3$H]dATP. The labelled, non-biotinylated denatured DNA [2000 ng to 5 ng] was applied to DDA-coated polystyrene plates. The test samples or plates were not allowed to dry. After incubation at 37° C. for periods of 30 minutes, 1 hour, 2 hours, 3 hours, 4 hours, and 18 hours, samples were counted. Binding was maximal after two hours of incubation, however, 50 percent of the originally applied DNA bound regardless of the concentration, thereby indicating that there is an equilibrium between bound and unbound DNA.

In other tests, polystyrene microfilter wells were nitrated using the procedure of Filipsson and Hornby, *Biochem. J.* 120, 215 (1970). The polystyrene wells were immersed for 20 minutes in a mixture of concentrated nitric and sulfuric acid [41 percent, v/v] cooled to 0° C. The wells were then washed thoroughly with water and subsequently heated to 70° C. in a 6 percent solution of sodium dithionate in 2 M potassium hydroxide. After 4 hours, the wells were washed thoroughly with 0.5 M hydrochloric acid and distilled water.

To produce 6-aminohexane linked polystyrene, 6-aminocaproic acid-N-hydroxysuccinimide ester·hydrobromide [5 mg thereof dissolved in 0.2 M dimethylformamide prepared by reacting 6-aminocaproic acid·hydrobromide with N-hydroxysuccinimide and dicyclohexyl carbodiimide in dimethylformamide and recrystallized from isopropylalcohol] was added to 0.1 M sodium borate [0.4 ml]. Amino-derivitized polystyrene microfilter wells filled with this solution were allowed to react at room temperature for 4 hours and then washed thoroughly with distilled water. The resulting treated wells absorbed H-labeled DNA from aqueous solution at pH less than 9.5.

An improved capability for fixing or immobilization of DNA to non-porous siliceous solid supports, such as glass and plastic, is also provided by treatment with a coating of an epoxy resin. For example, treatment of glass or polystyrene surfaces with commercially available epoxy glues, such as a solution of epoxy glue in ethanol [1 percent w/v] serves this purpose. These epoxy solutions are applied to the surfaces or wells, and the solvent, ethanol, evaporated thereupon at a temperature of 37° C., thereby providing a polyamine polymeric coating on the treated surface. These surfaces were found to absorb $^3$H-labeled DNA from aqueous solution at pH less than 9.5.

EXAMPLE 7

Yet another example of the method of the present invention, including fixing the polynucleotide analyte sequence directly to a non-porous solid support, such as a conventional microtiter well, may be performed according to the procedures outlined below.

Conventional microtiter well plates can be pre-rinsed with 1 M ammonium acetate (NH$_4$OAc), in an amount of 200 μls/well. Analyte DNA would be diluted to 10–200 ng/50 ul in water or 10 mM Tris-HCl at pH 7.5 and 1 mM EDTA(TE). After boiling for 5 minutes and quick cooling in ice water, an equal volume of 2M NH$_4$OAc would be added and 50 ul of analyte DNA is added per well, giving 5–100 ng of analyte DNA per well. After open plate incubation for 2 hours at 37° C., the wells can be sealed and plates stored at 4° C. Alternatively, open plates can be incubated at 37° C. until the wells are dry, at which point the plates can be sealed, and stored at 4° C. for up to one-two months. Single-stranded analyte DNA is now fixed to the wells.

An alternative method to denature and then fix the analyte DNA to the well is to add 50 ul of DNA in TE to wells at a concentration of 10–200 ng/50 ul. After adding 25 ul at 0.9 N NaOH and mixing, the plates can be incubated for 10 minutes at room temperature. After adding 25ul of 4 M NH$_4$OAc, the open plate may be incubated at 37° C. for 4 hours or until dry and the plates sealed and stored at 4° C. until ready to use.

To prepare the plates for hybridization, the wells would be rinsed twice with 0.3 m NaCl, 0.03 m sodium citrate (2X SSC) (200 ul/well) buffer regardless of whether the plate was dried or not. Preferably, the wells can be rinsed once with 2X SSC/1% Triton X-100 after the two 2X SSC rinses. Plates should be blotted on absorbent paper before beginning each rinse.

To hybridize the fixed analyte with a probe, the following protocol would be followed. A nick translated probe would be heat denatured and added to a hybridization solution containing 30% formamide (deionized), 2X–4X SSPE (20X SSPE=3.6 M NaCl, 0.2 M NaPO$_4$, pH 7.4, 0.02 M EDTA) depending on the GC content of probe, 0.1% SDS, and 5.0% dextran sulfate to give a final concentration of 0.2–1.0 ug probe/ml. An alternative hybridization solution contains 30% formamide (deionized), 2X–4X SSPE, 1.0% Triton X-100, and 5.0% dextran sulfate and 0.2–1.0 ug probe/ml. 100 ul of the selected hybridization mixture is added to each well. After sealing the plates, they are incubated at 37° C. for a desired time.

The hybridization solution is poured out, or collected by aspiration for reuse if desired. The plates are rinsed twice with 2X SSC and 0.1% SDS or 2X SSC and 0.10% Triton X-100 according to whether the first or second hybridization solution identified above was employed. At this point two to four stringency rinses of SSC and detergent are preferably performed by heating the buffer to the desired temperature and adding it hot to the wells. Formamide and low SSC or SSPE can be used at 37–40° C. to achieve the desired stringency. Following stringency washes, wells are rinsed twice with 1X SSC or 1X SSC and 0.1% Triton X-100, and the plates are now ready for detection.

Detection of the fixed hybridized analyte-probe according to the invention may employ the procedure for commercially available ELISA assays using the sensitive DETEK® 1-alkaline phosphatase or DETEK® 1-horseradish peroxidase assays (Enzo Biochem, Inc.). Beginning at the blocking procedure, the standard method is employed except that after blocking, no rinsing step is used. Complex diluted in 1X complex dilution buffer is thereafter added as taught in these commercially available assays.

As will be apparent to those skilled in the art in the light of the foregoing disclosure, many alterations, modifications and substitutions are possible in the practice of this invention, without departing from the spirit or scope thereof. Consequently, only such limitations as appear in the appended claims should be placed upon the scope of the invention.

The invention claimed is:

1. A non-porous solid support comprising one or more amine(s), hydroxyl(s) or epoxide(s) thereon, wherein at least one single-stranded nucleic acid is fixed or immobilized in hybridizable form to said non-porous solid support via said one or more amine(s), hydroxyl(s) or epoxide(s).

2. A non-porous solid support comprising one or more amine(s), hydroxyl(s) or epoxide(s) thereon, wherein at least one double-stranded nucleic acid is fixed or immobilized to said non-porous solid support via said one or more amine(s), hydroxyl(s) or epoxide(s), and wherein one nucleic acid strand of said at least one double-stranded nucleic acid has covalently attached thereto either:
   (i) a non-radioactive signaling moiety, or
   (ii) a non-radioactive bridging moiety covalently or non-covalently attached to a non-radioactive signaling moiety.

3. A non-porous solid support comprising at least one double-stranded nucleic acid fixed or immobilized thereto, wherein one nucleic acid strand of said at least one double-stranded nucleic acid has covalently attached thereto either:
   (i) a non-radioactive signaling moiety, or
   (ii) a non-radioactive bridging moiety covalently or non-covalently attached to a non-radioactive signaling moiety,
and wherein said fixation or immobilization is not to a cell fixed in situ to said non-porous solid support.

4. A non-porous solid support comprising one or more amine(s), hydroxyl(s) or epoxide(s) thereon, and at least one nucleic acid strand or sequence fixed or immobilized to said non-porous solid support via said one or more amine(s), hydroxyl(s) or epoxide(s), and wherein another nucleic acid strand or sequence is hybridized to said at least one nucleic acid strand or sequence, said another nucleic acid strand or sequence having covalently attached thereto either:
   (l) a non-radioactive signaling moiety, or
   (ll) a non-radioactive bridging moiety covalently or non-covalently attached to a non-radioactive signaling moiety.

5. A non-porous solid support comprising at least one nucleic acid strand or sequence fixed or immobilized to said non-porous solid support, and wherein one other nucleic acid strand or sequence is hybridized to said at least one nucleic acid strand or sequence, said other nucleic acid strand or sequence having covalently attached thereto either:
   (i) a non-radioactive signaling moiety, or
   (ii) a non-radioactive bridging moiety covalently or non-covalently attached to a non-radioactive signaling moiety,
and wherein said fixation or immobilization is not to a cell fixed in situ to said non-porous solid support.

6. A system comprising a non-porous solid support which comprises one or more amine(s), hydroxyl(s) or epoxide(s) thereon, wherein at least one single-stranded nucleic acid is fixed or immobilized thereto in hybridizable form to said non-porous solid support via said one or more amine(s), hydroxyl(s) or epoxide(s).

7. A system comprising a non-porous solid support which comprises one or more amine(s), hydroxyl(s) or epoxide(s) thereon, wherein at least one double-stranded nucleic acid is fixed or immobilized to said non-porous solid support via said one or more amine(s), hydroxyl(s) or epoxide(s), and wherein one nucleic acid strand of said double-stranded nucleic acid has covalently attached thereto either:
   (l) a non-radioactive signaling moiety, or
   (ii) a non-radioactive bridging moiety covalently or non-covalently attached to a non-radioactive signaling moiety.

8. A system comprising a non-porous solid support which comprises one or more amine(s), hydroxyl(s) or epoxide(s) thereon, wherein DNA or RNA is fixed or immobilized in hybridizable form to said non-porous solid support via said one or more amine(s), hydroxyl(s) or epoxide(s).

9. A system comprising a non-porous solid support which comprises one or more amine(s), hydroxyl(s) or epoxide(s) thereon, wherein nucleic acid is fixed or immobilized in hybridizable form to said non-porous solid support via said one or more amine(s), hydroxyl(s) or epoxide(s).

10. A system comprising a non-porous solid support which comprises double-stranded nucleic acid fixed or immobilized thereto, wherein one nucleic acid strand of said double-stranded nucleic acid has covalently attached thereto either:
    (i) a non-radioactive signaling moiety, or
    (ii) a non-radioactive bridging moiety covalently or non-covalently attached to a non-radioactive signaling moiety,
and wherein said fixation or immobilization is not to a cell fixed in situ to said non-porous solid support.

11. A system comprising a non-porous solid support which comprises a double-stranded nucleic acid fixed or immobilized thereto, wherein one nucleic acid strand of said double-stranded nucleic acid has covalently attached thereto either:
    (i) a non-radioactive signaling moiety, or
    (ii) a non-radioactive bridging moiety covalently or non-covalently attached to a non-radioactive signaling moiety,
and wherein said fixation or immobilization is not to a cell fixed in situ to said non-porous solid support.

12. A non-porous solid support comprising one or more amine(s), hydroxyl(s) or epoxide(s) thereon, wherein single-stranded nucleic acid is fixed or immobilized in hybridizable form to said non-porous solid support via said one or more amine(s), hydroxyl(s) or epoxide(s).

13. A non-porous solid support comprising one or more amine(s), hydroxyl(s) or epoxide(s) thereon, wherein a single-stranded nucleic acid is fixed or immobilized in hybridizable form to said non-porous solid support via said one or more amine(s), hydroxyl(s) or epoxide(s).

14. A non-porous solid support comprising one or more amine(s), hydroxyl(s) or epoxide(s) thereon, wherein nucleic acid is fixed or immobilized in hybridizable form to said non-porous solid support via said one or more amine(s), hydroxyl(s) or epoxide(s).

15. A non-porous solid support comprising one or more amine(s), hydroxyl(s) or epoxide(s) thereon, wherein DNA or RNA is fixed or immobilized in hybridizable form to said non-porous solid support via said one or more amine(s), hydroxyl(s).

16. The non-porous solid support of claims 1, 2, 12, 13, 14, 15 or 4, wherein said fixation or immobilization is not to a cell fixed in situ to said non-porous solid support.

17. An array comprising various single-stranded nucleic acids fixed or immobilized in hybridizable form to a non-porous solid support.

18. An array comprising various double-stranded nucleic acids fixed or immobilized to a non-porous solid support, wherein at least one nucleic acid strand of said various double-stranded nucleic acids comprises at least one non-radioactive signaling moiety which is quantifiable or detectable.

19. An array comprising single-stranded nucleic acids fixed or immobilized in hybridizable form to a non-porous solid support.

20. An array comprising double-stranded nucleic acids fixed or immobilized to a non-porous solid support, wherein at least one nucleic acid strand of said double-stranded nucleic acids comprises at least one non-radioactive signaling moiety which is quantifiable or detectable.

21. An array comprising various nucleic acids, wherein single-stranded nucleic acids or sequences are fixed or immobilized to a non-porous solid support, and other single-stranded nucleic acids or sequences are hybridized to said fixed or immobilized single-stranded nucleic acids or sequences, said other nucleic acid strands or sequences comprising at least one non-radioactive signaling moiety which is quantifiable or detectable.

22. An array comprising various first single-stranded nucleic acids fixed or immobilized to a non-porous solid support, and further comprising second nucleic acids hybridized to said fixed or immobilized first nucleic acids, wherein said second nucleic acids comprise at least one non-radioactive signalling moiety which is quantifiable or detectable.

23. The non-porous solid support of claims 1, 2, 12, 13, 14, 15, 3, 4 or 5, wherein said non-porous solid support comprises an arrangement of wells, tubes or cuvettes.

24. The non-porous solid support of claim 3 or 5, comprising one or more amines.

25. An array comprising various single-stranded nucleic acids fixed or immobilized in hybridizable form to a non-porous solid support having wells or depressions.

26. An array comprising various double-stranded nucleic acids fixed or immobilized to a non-porous solid support having wells or depressions, wherein at least one nucleic acid strand of each of said various double-stranded nucleic acids comprises at least one non-radioactive signaling moiety which is quantifiable or detectable.

27. A non-porous glass or non-porous plastic solid support comprising one or more amine(s), hydroxyl(s) or epoxide(s) thereon, wherein at least one single-stranded nucleic acid is fixed or immobilized in hybridizable form to said non-porous solid support via said one or more amine(s), hydroxyl(s) or epoxide(s).

28. A non-porous glass or non-porous plastic solid support comprising one or more amine(s), hydroxyl(s) or epoxide(s) thereon, wherein at least one double-stranded nucleic acid is fixed or immobilized to said non-porous glass or non-porous plastic solid support via said one or more amine(s), hydroxyl(s) or epoxide(s), and wherein one nucleic acid strand of said double-stranded nucleic acid has covalently attached thereto either:
    (i) a non-radioactive signaling moiety, or
    (ii) a non-radioactive bridging moiety covalently or non-covalently attached to a non-radioactive signaling moiety.

29. A non-porous solid support comprising double-stranded nucleic acid fixed or immobilized thereto, wherein one nucleic acid strand of said double-stranded nucleic acid has covalently attached thereto either:
    (i) a non-radioactive signaling moiety, or
    (ii) a non-radioactive bridging moiety covalently or non-covalently attached to a non-radioactive signaling moiety,
wherein said fixation or immobilization is not to a cell fixed in situ to said non-porous solid support.

30. A non-porous solid support comprising a double-stranded nucleic acid fixed or immobilized thereto, wherein one nucleic acid strand of said double-stranded nucleic acid has covalently attached thereto either:
    (i) a non-radioactive signaling moiety, or
    (ii) a non-radioactive bridging moiety covalently or non-covalently attached to a non-radioactive signaling moiety,
wherein said fixation or immobilization is not to a cell fixed in situ to said non-porous solid support.

31. The non-porous solid support of claim 1, wherein said nucleic acid comprises a nucleic acid sequence complementary to a nucleic acid sequence of interest sought to be identified, quantified or sequenced.

32. The non-porous solid support of claims 1, 2, 3, 4 or 5, wherein said non-porous solid support comprises glass or plastic.

33. The non-porous solid support of claims 1, 2, 3, 4 or 5, wherein said non-porous solid support comprises a plate or plates, a well or wells, a microtiter well or microtiter wells, a depression or depressions, a tube or tubes, or a cuvette or cuvettes.

34. The non-porous solid support of claims 1, 2, 3, 4 or 5, wherein said non-porous solid support has been treated with a surface treatment agent, a blocking agent, or both.

35. The non-porous solid support of claim 34, wherein said surface treatment agent comprises an amine providing compound, an epoxy glue or solution, an acid solution, or ammonium acetate.

36. The non-porous solid support of claim 34, wherein said blocking agent comprises Denhardt's solution.

37. The non-porous solid support of claim 35, wherein said acid compound comprises nitric acid.

38. The non-porous solid support of claims 1, 2, 3, 4 or 5, wherein said fixation or immobilization to said non-porous solid support is covalent.

39. The non-porous solid support of claims 1, 2, 3, 4 or 5, wherein said non-porous solid support is transparent or translucent.

40. The non-porous solid support of claims 1, 2, 3, 4 or 5, wherein said non-porous solid support comprises a plate or plates.

41. The non-porous solid support of claims 1, 2, 3, 4 or 5, wherein said non-porous solid support comprises a well or wells, a microtiter well or microtiter wells, or a depression or depressions.

42. The non-porous solid support of claim 35, wherein said amine providing compound comprises dodecadiamine (DDA), polylysine (PPL) or 6-aminohexane.

43. The non-porous solid support of claims 2, 3 or 5, wherein one strand of said at least one double-stranded nucleic acid is fixed or immobilized to said non-porous solid support and the other strand of said at least one double-stranded nucleic acid is hybridized to said one strand.

44. The non-porous solid support of claims 2, 3 or 5, wherein said nucleic acid is DNA.

45. The non-porous solid support of claims 2, 3 or 5, wherein said non-radioactive signaling moiety comprises a chromagen or a chromagenic compound.

46. The non-porous solid support of claims 2, 3 or 5, wherein a non-radioactive signal from said non-radioactive signaling moiety is quantifiable or detectable by photometric techniques.

47. The non-porous solid support of claims 2, 3 or 5, comprising more than one double-stranded nucleic acid.

48. The non-porous solid support of claims 2, 3 or 5, wherein said nucleic acid is RNA.

49. The non-porous solid support of claims 2, 3 or 5, wherein said nucleic acid comprises both DNA and RNA.

50. The non-porous solid support of claims 2, 3 or 5, wherein said non-radioactive signaling moiety is a colored dye compound.

51. The non-porous solid support of claims 2, 3 or 5, wherein said non-radioactive signaling moiety is a fluorogen or a fluorescent compound.

52. The non-porous solid support of claims 2, 3 or 5, wherein said non-radioactive signaling moiety is a chemiluminescent compound.

53. The non-porous solid support of claims 2, 3 or 5, wherein said non-radioactive signaling moiety comprises a chelating compound.

54. The non-porous solid support of claims 2, 3 or 5, wherein said non-radioactive signaling moiety comprises an enzyme or an enzymatic compound.

55. The non-porous solid support of claims 2, 3 or 5, wherein said non-radioactive signaling moiety comprises a coenzyme.

56. The non-porous solid support of claims 2, 3 or 5, wherein said non-radioactive signaling moiety comprises a biotin.

57. The non-porous solid support of claims 2, 3 or 5, wherein a non-radioactive signal from said non-radioactive signaling moiety is quantifiable or detectable by spectrophotometric techniques.

58. The non-porous solid support of claims 2, 3 or 5, wherein a non-radioactive signal from said non-radioactive signaling moiety is quantifiable or detectable by colorimetric techniques.

59. The non-porous solid support of claims 2, 3 or 5, wherein a non-radioactive signal from said non-radioactive signaling moiety is quantifiable or detectable by fluorometric techniques.

60. The non-porous solid support of claims 2, 3 or 5, wherein a non-radioactive signal from said non-radioactive signaling moiety is quantifiable or detectable by chemiluminescent techniques.

61. The non-porous solid support of claims 1 or 4, wherein said nucleic acid is DNA.

62. The non-porous solid support of claims 1 or 4, wherein said single-stranded nucleic acid is unlabeled.

63. The non-porous solid support of claims 1 or 4, comprising more than one single-stranded nucleic acid.

64. The non-porous solid support of claims 1 or 4, wherein said nucleic acid is RNA.

65. The non-porous solid support of claims 2 or 3, wherein one strand of said at least one double-stranded nucleic acid comprises a nucleic acid sequence of interest sought to be identified, quantified or sequenced.

66. The non-porous solid support of claims 2 or 3, wherein said non-radioactive signaling moiety is quantifiable in or from a fluid or solution, said quantity being proportional to the amount or quantity of said non-radioactive signaling moiety.

67. The non-porous solid support of claims 2 or 3, wherein said non-porous solid support is transparent or translucent, and said non-radioactive signaling moiety is quantifiable in or from a fluid or solution or from said non-porous solid support, said quantity being proportional to the amount or quantity of said non-radioactive signaling moiety.

68. The system of claim 6, wherein said nucleic acid comprises a nucleic acid sequence complementary to a nucleic acid sequence of interest sought to be identified, quantified or sequenced.

69. The system of claim 6, wherein said single-stranded nucleic acid is unlabeled.

70. The system of claim 6, comprising more than one single-stranded nucleic acid.

71. The system of claim 7, wherein said bridging moiety comprises biotin-avidin, biotin-streptavidin or sugar-lectin.

72. The system of claims 6, 7, 8, 9, 10 or 11, wherein said non-porous solid support comprises glass or plastic.

73. The system of claims 6, 7, 8, 9, 10, or 11, wherein said non-porous solid support comprises a plate or plates, a well or wells, a microtiter well or microtiter wells, a depression or depressions, a tube or tubes, or a cuvette or cuvettes.

74. The system of claims 6, 7, 8, 9, 10 or 11, wherein said non-porous solid support has been treated with a surface treatment agent, a blocking agent, or both.

75. The system of claim 74, wherein said surface treatment agent comprises an amine providing compound, an epoxy glue or solution, an acid solution or ammonium acetate.

76. The system of claim 75, wherein said acid compound comprises nitric acid.

77. The system of claim 74, wherein said blocking agent comprises Denhardt's solution.

78. The system of claims 6, 7, 8, 8, 10 or 11, wherein said fixation or immobilization to said non-porous solid support is covalent.

79. The system of claims 6, 7, 8, 9, 10 or 11, wherein said fixation or immobilization to said non-porous solid support is non-covalent.

80. The system of claims 6, 7, 8, 9, 10 or 11 wherein said non-porous solid support is transparent or translucent.

81. The system of claims 7, 10 or 11, wherein one strand of said double-stranded nucleic acid is fixed or immobilized to said non-porous solid support and the other nucleic acid strand of said double-stranded nucleic acid is hybridized to said one strand.

82. The system of claims 7, 10 or 11, wherein said nucleic acid is DNA.

83. The system of claims 7, 10 or 11, wherein said non-radioactive signaling moiety comprises a chromagen or a chromagenic compound.

84. The system of claims 7, 10 or 11, wherein a non-radioactive signal from said non-radioactive signaling moiety is quantifiable or detectable by photometric techniques.

85. The system of claims 7, 10 or 11, comprising more than one double-stranded nucleic acid.

86. The system of claims 7, 10 or 11, wherein one strand of said double-stranded nucleic acid is fixed or immobilized to said non-porous solid support and the other strand of said double-stranded nucleic acid is hybridized to said one strand.

87. The system of claims 7, 10 or 11, wherein said nucleic acid comprises RNA.

88. The system of claims 7, 10 or 11, wherein said nucleic acid comprises both DNA and RNA.

89. The system of claims 7, 10 or 11, wherein said non-radioactive signaling moiety comprises a colored dye compound.

90. The system of claims 7, 10 or 11, wherein said non-radioactive signaling moiety comprises a fluorogen or a fluorescent compound.

91. The system of claims 7, 10 or 11, wherein said non-radioactive signaling moiety comprises a chemiluminescent compound.

92. The system of claims 7, 10 or 11, wherein said non-radioactive signaling moiety comprises a chelating compound.

93. The system of claims 7, 10 or 11, wherein said non-radioactive signaling moiety comprises an enzyme or an enzymatic compound.

94. The system of claims 7, 10 or 11, wherein said non-radioactive signaling moiety comprises a coenzyme.

95. The system of claims 7, 10 or 11, wherein said non-radioactive signaling moiety comprises a biotin.

96. The system of claims 7, 10 or 11, wherein a non-radioactive signal from said non-radioactive signaling moiety is quantifiable or detectable by spectrophotometric techniques.

97. The system of claims 7, 10 or 11, wherein a non-radioactive signal from said non-radioactive signaling moiety is quantifiable or detectable by colorimetric techniques.

98. The system of claims 7, 10 or 11, wherein a non-radioactive signal from said non-radioactive signaling moiety is quantifiable or detectable by fluorometric techniques.

99. The system of claims 7, 10 or 11, wherein a non-radioactive signal from said non-radioactive signaling moiety is quantifiable or detectable by chemiluminescent techniques.

100. The system of claims 6 or 9, wherein said nucleic acid is DNA.

101. The system of claims 6 or 9, wherein said nucleic acid is RNA.

102. The system of claims 7 or 16, wherein one strand of said at least one double-stranded nucleic acid comprises a nucleic acid sequence of interest sought to be identified, quantified or sequenced.

103. The system of claims 7 or 16, wherein said non-radioactive signaling moiety is quantifiable in or from a fluid or solution, said quantity being proportional to the amount or quantity of said non-radioactive signaling moiety.

104. The system of claims 7 or 16, wherein said non-porous solid support is transparent or translucent, and said non-radioactive signaling moiety is quantifiable in or from a fluid or solution or from said non-porous solid support, said quantity being proportional to the amount or quantity of said non-radioactive signaling moiety.

105. The array of claims 17, 18, 19, 20, 21 or 22, wherein said non-porous solid support comprises glass or plastic.

106. The array of claims 17, 18, 19, 20, 21 or 22, wherein said non-porous solid support comprises a plate or plates, a well or wells, a microtiter well or microtiter wells, a depression or depressions, a tube or tubes, or a cuvette or cuvettes.

107. The array of claims 17, 18, 19, 20, 21 or 22, comprising one or more amines.

108. The array of claims 17, 18, 19, 20, 21 or 22, wherein said non-porous solid support has been treated with a surface treatment agent, a blocking agent, or both.

109. The array of claim 108, wherein said surface treatment agent comprises an amine providing compound, an epoxy glue or solution, an acid solution or ammonium acetate.

110. The array of claim 109, wherein said amine providing compound comprises dodecadiamine (DDA), polylysine (PPL) or 6-aminohexane.

111. The array of claim 109, wherein said acid compound comprises nitric acid.

112. The array of claim 108, wherein said blocking agent comprises Denhardt's solution.

113. The array of claims 17, 18, 19, 20, 21 or 22, wherein said fixation or immobilization to said non-porous solid support is covalent.

114. The array of claims 17, 18, 19, 20, 21 or 22, wherein said fixation or immobilization to said non-porous solid support is non-covalent.

115. The array of claims 17, 18, 19, 20, 21 or 22, wherein said non-porous solid support is transparent or translucent.

116. The array of claims 17, 18, 19, 20, 21 or 22, wherein said fixation or immobilization is not to a cell fixed in situ to said non-porous solid support.

117. The array of claims 17, 18, 19, 20, 21 or 22, wherein said non-porous solid support comprises an arrangement of wells, tubes or cuvettes.

118. The array of claims 17, 18, 19, 20, 21 or 22, wherein said non-porous solid support comprises a plate or plates.

119. The array of claims 17, 18, 19, 20, 21 or 22, wherein said non-porous solid support comprises a well or wells, a microtiter well or microtiter wells, or a depression or depressions.

120. The array of claim 17, 18, 19, 20, 21 or 22, wherein said non-porous solid support comprises one or more hydroxyls.

121. The array of claim 17, 18, 19, 20, 21 or 22, wherein said non-porous solid support comprises one or more epoxides.

122. The array of claims 18 or 20, wherein the first strands of said double-stranded nucleic acids are fixed or immobilized to said non-porous solid support and the other nucleic acid strands of said double-stranded nucleic acids are hybridized to said first strands.

123. The array of claims 18 or 20, wherein said nucleic acids is DNA.

124. The array of claims 18 or 20, wherein the first strands of said double-stranded nucleic acids are fixed or immobilized to said non-porous solid support and the other nucleic acid strands of said double-stranded nucleic acids are hybridized to said first strands.

125. The array of claims 18 or 20, wherein one strand of said at least one double-stranded nucleic acid is fixed or immobilized to said non-porous solid support by sandwich hybridization.

126. The array of claims 18 or 20, wherein said nucleic acids is RNA.

127. The array of claims 18 or 02, wherein said nucleic acids comprises both DNA and RNA.

128. The array of claims 17 or 19, wherein said nucleic acids is DNA.

129. The array of claims 17 or 19, wherein said single-stranded nucleic acids are unlabeled.

130. The array of claims 17 or 19, wherein said nucleic acids is RNA.

131. The array of claims 17 or 23, wherein said nucleic acids comprise nucleic acid sequences complementary to nucleic acid sequences of interest sought to be identified, quantified or sequenced.

132. The array of claims 18 or 24, wherein one strand of said double-stranded nucleic acids comprises a nucleic acid sequence of interest sought to be identified, quantified or sequenced.

133. The array of claims 18 or 24, wherein said non-radioactive signaling moiety is quantifiable in or from a fluid or solution, said quantity being proportional to the amount or quantity of said label or labels.

134. The array of claims 18 or 42, wherein said non-porous solid support is transparent or translucent, and said non-radioactive signaling moiety is quantifiable in or from a fluid or solution or from said non-porous solid support, said quantity being proportional to the amount or quantity of said non-radioactive signaling moiety.

135. The array of claims 18, 20, 21 or 22, wherein said non-radioactive signaling moiety comprises a chromagen or a chromagenic compound.

136. The array of claims 18, 20, 21 or 22, wherein a non-radioactive signal from said non-radioactive signaling moiety is quantifiable or detectable by photometric techniques.

137. The array of claims 18, 20, 21 or 22, wherein said non-radioactive signaling moiety is attached to said at least one nucleic acid strand through a bridging moiety.

138. The array of claim 137, wherein said bridging moiety comprises biotin-avidin, biotin-streptavidin or sugar-lectin.

139. The array of claims 18, 20, 21 or 22, wherein said non-radioactive signaling moiety is a colored dye compound.

140. The array of claims 18, 20, 21 or 22, wherein said non-radioactive signaling moiety is a fluorogen or a fluorescent compound.

141. The array of claims 18, 20, 21 or 22, wherein said non-radioactive signaling moiety is a chemiluminescent compound.

142. The array of claims 18, 20, 21 or 22, wherein said non-radioactive signaling moiety is a chelating compound.

143. The array of claims 18, 20, 21 or 22, wherein said non-radioactive signaling moiety is an enzyme or an enzymatic compound.

144. The array of claims 18, 20, 21 or 22, wherein said non-radioactive signaling moiety is a coenzyme.

145. The array of claims 18, 20, 21 or 22, wherein said non-radioactive signaling moiety is biotin.

146. The array of claims 18, 20, 21 or 22, wherein a non-radioactive signal from said non-radioactive signaling moiety is quantifiable or detectable by spectrophotometric techniques.

147. The array of claims 18, 20, 21 or 22, wherein a non-radioactive signal from said non-radioactive signaling moiety is quantifiable or detectable by colorimetric techniques.

148. The array of claims 18, 20, 21 or 22, wherein a non-radioactive signal from said non-radioactive signaling moiety is quantifiable or detectable by fluorometric techniques.

149. The array of claims 18, 20, 21 or 22, wherein a non-radioactive signal from said non-radioactive signaling moiety is quantifiable or detectable by chemiluminescent techniques.

150. The array of claim 25, wherein said nucleic acids are DNA.

151. The array of claim 25, wherein said nucleic acids comprise a gene sequence or pathogen sequence.

152. The array of claim 25, wherein said single-stranded nucleic acids are unlabeled.

153. The array of claims 25 or 26, wherein said non-porous solid support is transparent or translucent.

154. The array of claim 25, wherein said nucleic acids are RNA.

155. The array of claim 26, wherein the first strands of said double-stranded nucleic acids are fixed or immobilized to said non-porous solid support and the other nucleic acid strands of said double-stranded nucleic acids are hybridized to said first strands.

156. The array of claim 26, wherein said nucleic acids are DNA.

157. The array of claim 26, wherein one strand of said double-stranded nucleic acids comprises a gene sequence or pathogen sequence.

158. The array of claim 26, wherein said non-radioactive signaling moiety is quantifiable in or from a fluid or solution, said quantity being proportional to the amount or quantity of said non-radioactive signaling moiety.

159. The array of claim 26, wherein said non-porous solid support is transparent or translucent, and said non-radioactive signaling moiety is quantifiable in or from a fluid or solution or from said non-porous solid support, said quantity being proportional to the amount or quantity of said non-radioactive signaling moiety.

160. The array of claim 26, wherein said non-radioactive signaling moiety comprises a chromagen or a chromagenic compound.

161. The array of claim 26, wherein a non-radioactive signal from said non-radioactive signaling moiety is quantifiable or detectable by photometric techniques.

162. The array of claim 26, wherein said at least one non-radioactive signaling moiety is attached to said at least one nucleic acid strand through a bridging moiety.

163. The array of claim 162, wherein said bridging moiety comprises biotin-avidin, biotin-streptavidin or sugar-lectin.

164. The array of claim 26, wherein one strand of various double-stranded nucleic acids is fixed or immobilized to said non-porous solid support by sandwich hybridization.

165. The array of claim 26, wherein said nucleic acids are RNA.

166. The array of claim 26, wherein said nucleic acids comprise both DNA and RNA.

167. The array of claim 26, wherein said non-radioactive signaling moiety comprises a colored dye compound.

168. The array of claim 26, wherein said non-radioactive signaling moiety comprises a fluorescent compound.

169. The array of claim 26, wherein said non-radioactive signaling moiety comprises a chemiluminescent compound.

170. The array of claim 26, wherein said non-radioactive signaling moiety comprises a chelating compound.

171. The array of claim 26, wherein said non-radioactive signaling moiety comprises an enzyme or an enzymatic compound.

172. The array of claim 26, wherein said non-radioactive signaling moiety comprises a coenzyme.

173. The array of claim 26, wherein said non-radioactive signaling moiety comprises a biotin.

174. The array of claim 26, wherein a non-radioactive signal from said non-radioactive signaling moiety is quantifiable or detectable by spectrophotometric techniques.

175. The array of claim 26, wherein a non-radioactive signal from said non-radioactive signaling moiety is quantifiable or detectable by colorimetric techniques.

176. The array of claim 26, wherein a non-radioactive signal from said non-radioactive signaling moiety is quantifiable or detectable by fluorometric techniques.

177. The array of claim 26, wherein a non-radioactive signal from said non-radioactive signaling moiety is quantifiable or detectable by chemiluminescent techniques.

178. The array of claims 25 or 26, wherein said non-porous solid support comprises glass or plastic.

179. The array of claims 25 or 26, wherein said non-porous solid support comprises one or more amines.

180. The array of claims 25 or 26, wherein said non-porous solid support has been treated with a surface treatment agent, a blocking agent, or both.

181. The array of claim 180, wherein said surface treatment agent comprises an amine providing compound, an epoxy glue or solution, an acid solution or ammonium acetate.

182. The array of claim 181, wherein said amine providing compound comprises dodecadiamine (DDA), polylysine (PPL) or 6-aminohexane.

183. The array of claim 181, wherein said acid compound comprises nitric acid.

184. The array of claim 180, wherein said blocking agent comprises Denhardt's solution.

185. The array of claims 25 or 26, wherein said fixation or immobilization to said non-porous solid support is covalent.

186. The array of claims 25 or 26, wherein said fixation or immobilization to said non-porous solid support is non-covalent.

187. The array of claims 25 or 26, wherein said fixation or immobilization is not to a cell fixed in situ to said non-porous solid support.

188. The array of claims 25 or 26, wherein said non-porous solid support comprises an arrangement of said wells.

189. The array of claim 25 or 26, wherein said non-porous solid support comprises one or more hydroxyls.

190. The array of claim 25 or 26, wherein said non-porous solid support comprises one or more epoxides.

191. The non-porous glass or non-porous plastic solid support of claim 27, wherein said nucleic acid is DNA.

192. The non-porous glass or non-porous plastic solid support of claim 27, wherein said nucleic acid comprises a nucleic acid sequence complementary to a nucleic acid sequence of interest sought to be identified, quantified or sequenced.

193. The non-porous glass or non-porous plastic solid support of claim 27, wherein said single-stranded nucleic acid is unlabeled.

194. The non-porous glass or non-porous plastic solid support of claim 27, comprising more than one single-stranded nucleic acid fixed or immobilized in hybridizable form to said non-porous glass or non-porous plastic solid support.

195. The non-porous glass or non-porous plastic solid support of claim 27, wherein said nucleic acid is RNA.

196. The non-porous glass or non-porous plastic solid support of claim 28, wherein said nucleic acid is DNA.

197. The non-porous glass or non-porous plastic solid support of claim 28, wherein one strand of said at least one double-stranded nucleic acid comprises a nucleic acid sequence of interest sought to be identified, quantified or sequenced.

198. The non-porous glass or non-porous plastic solid support of claim 28, wherein said non-radioactive signaling moiety is quantifiable in or from a fluid or solution, said quantity being proportional to the amount or quantity of said label or labels.

199. The non-porous glass or non-porous plastic solid support of claim 28, comprising more than one double-stranded nucleic acid fixed or immobilized in hybridizable form to said non-porous glass or non-porous plastic solid support.

200. The non-porous glass or non-porous plastic solid support of claim 28, wherein said bridging moiety comprises biotin-avidin, biotin-streptavidin or sugar-lectin.

201. The non-porous glass or non-porous plastic solid support of claim 28, wherein said non-radioactive signaling moiety comprises a chromagen or a chromagenic compound.

202. The non-porous glass or non-porous plastic solid support of claim 28, wherein one strand of said at least one double-stranded nucleic acid is fixed or immobilized to said non-porous solid support by sandwich hybridization.

203. The non-porous glass or non-porous plastic solid support of claim 28, wherein said nucleic acid is RNA.

204. The non-porous glass or non-porous plastic solid support of claim 28, wherein said nucleic acid comprises both DNA and RNA.

205. The non-porous glass or non-porous plastic solid support of claim 28, wherein said non-radioactive signaling moiety comprises a colored dye compound.

206. The non-porous glass or non-porous plastic solid support of claim 28, wherein said non-radioactive signaling moiety comprises a fluorescent compound.

207. The non-porous glass or non-porous plastic solid support of claim 28, wherein said non-radioactive signaling moiety comprises a chemiluminescent compound.

208. The non-porous glass or non-porous plastic solid support of claim 28, wherein said non-radioactive signaling moiety comprises a chelating compound.

209. The non-porous glass or non-porous plastic solid support of claim 28, wherein said non-radioactive signaling moiety comprises an enzyme or an enzymatic compound.

210. The non-porous glass or non-porous plastic solid support of claim 28, wherein said non-radioactive signaling moiety comprises a coenzyme.

211. The non-porous glass or non-porous plastic solid support of claim 28, wherein said non-radioactive signaling moiety comprises a biotin.

212. The non-porous glass or non-porous plastic solid support of claims 27 or 28, wherein said non-porous glass or non-porous plastic solid support comprises a plate or plates, a well or wells, a microtiter well or microtiter wells, a depression or depressions, a tube or tubes, or a cuvette or cuvettes.

213. The non-porous glass or non-porous plastic solid support of claims 27 or 28, wherein said non-porous glass or non-porous plastic solid support has been treated with a surface treatment agent, a blocking agent, or both.

214. The non-porous glass or non-porous plastic solid support of claim 213, wherein said surface treatment agent comprises an amine providing compound, an epoxy glue or solution, an acid solution or ammonium acetate.

215. The non-porous glass or non-porous plastic solid support of claim 214, wherein said amine providing compound comprises dodecadiamine (DDA), polylysine (PPL) or 6-aminohexane.

216. The non-porous glass or non-porous plastic solid support of claim 214, wherein said acid compound comprises nitric acid.

217. The non-porous glass or non-porous plastic solid support of claim 213, wherein said blocking agent comprises Denhardt's solution.

218. The non-porous glass or non-porous plastic solid support of claims 27 or 28, wherein said fixation or immobilization to said non-porous glass or non-porous plastic solid support is covalent.

219. The non-porous glass or non-porous plastic solid support of claims 27 or 28, wherein said fixation or immobilization to said non-porous glass or non-porous plastic solid support is non-covalent.

220. The non-porous glass or non-porous plastic solid support of claim 28, wherein one strand of said double-stranded nucleic acid is fixed or immobilized to said non-porous glass or non-porous plastic solid support by sandwich hybridization or by hybridization to a complementary nucleic acid strand or sequence.

221. The non-porous glass or non-porous plastic solid support of claims 27 or 28, wherein said non-porous glass or non-porous plastic solid support is transparent or translucent.

222. The non-porous glass or non-porous plastic solid support of claims 27 or 28, wherein said fixation or immobilization is not to a cell fixed in situ to said non-porous solid support.

223. The non-porous glass or non-porous plastic solid support of claims 27 or 28, wherein said non-porous solid support comprises an arrangement of wells, tubes or cuvettes.

224. The non-porous glass or non-porous plastic solid support of claims 27 or 28, wherein said non-porous glass or non-porous plastic solid support comprises a plate or plates.

225. The non-porous glass or non-porous plastic solid support of claims 27 or 28, wherein said non-porous glass or non-porous plastic solid support comprises a well or wells, a microtiter well or microtiter wells, or a depression or depressions.

226. The non-porous solid support of claims 12, 13, 14, 15, 29 or 30, wherein said non-porous solid support comprises glass or plastic.

227. The system of claims 8, 9, 10 or 11, wherein said non-porous solid support comprises glass or plastic.

228. The non-porous solid support of claims 2, 29, 30, 3 or 5, wherein said bridging moiety comprises biotin-avidin, biotin-streptavidin or sugar-lectin.

229. The non-porous solid support of claims 2, 29, 30, 3 or 5, wherein one strand of said at least one double-stranded nucleic acid is fixed or immobilized to said non-porous solid support by sandwich hybridization.

230. The system of claims 6, 7, 8 or 9, wherein said fixation or immobilization is not to a cell fixed in situ to said non-porous solid support.

231. The system of claims 6, 7, 8, 9, 10 or 11, wherein said non-porous solid support comprises an arrangement of wells, tubes or cuvettes.

232. The system of claims 6, 7, 8, 9, 10 or 11, wherein said non-porous solid support comprises a plate or plates.

233. The system of claims 6, 7, 8, 9, 10 or 11, wherein said non-porous solid support comprises a well or wells, a microtiter well or microtiter wells, or a depression or depressions.

234. The non-porous solid support of claim 22 or 5, wherein said non-porous solid support comprises one or more hydroxyls.

235. The non-porous solid support of claim 3 or 5, wherein said non-porous solid support comprises one or more epoxides.

236. The non-porous solid support of claims 1, 2, 3, 4 or 5, wherein said fixation or immobilization to said non-porous solid support is non-covalent.

237. The non-porous glass or non-porous plastic solid support of claim 28, wherein said non-porous glass or non-porous plastic solid support is transparent or translucent, and non-radioactive signaling moiety is quantifiable in or from a fluid or solution or from said non-porous glass or non-porous plastic solid support, said quantity being proportional to the amount or quantity of said non-radioactive signaling moiety.

238. The system of claim 75, wherein said amine providing compound comprises dodecadiamine (DDA), polylysine (PPL) or 6-aminohexane.

* * * * *

UNITED STATES PATENT AND TRADEMARK OFFICE
CERTIFICATE OF CORRECTION

PATENT NO. : 7,064,197 B1 Page 1 of 1
APPLICATION NO. : 08/486070
DATED : June 20, 2006
INVENTOR(S) : Elazar Rabbani et al.

It is certified that error appears in the above-identified patent and that said Letters Patent is hereby corrected as shown below:

Front Page, After and Under
"(*) Notice: Subject to any disclaimer, the term of this patent is extended or adjusted under 35 U.S.C. 154(b) by 0 days."
delete the sentence "This patent is subject to a terminal disclaimer."
Col. 9, line 7, after "of any hybrid probe-analyte is" and before "detectable" insert -- then --.
Col. 9, line 7, after "One" and before "detection" delete "then".
Col. 9, line 8, before "technique as described" delete "- - -".
Col. 10, EXAMPLE 3, line 35, change "Triton X-100" to -- TRITON X-100 (octoxynol) --.
Col. 11, line 2, change "avidin" to -- avidin- --.
Col. 11, EXAMPLE 5, line 35, change "duodecadiamine" to -- dodecadiamine --.
Col. 12, EXAMPLE 6, line 32, change "isopropylalcohol" to -- isopropyl alcohol --.
Col. 13, EXAMPLE 7, line 17, change "Triton X-100" to -- TRITON X-100 (octoxynol) --.
Col. 13. lines 28-29, change "Triton X-100" to -- TRITON X-100 (octoxynol) --.
Col. 13. lines 35-36, change "Triton X-100" to -- TRITON X-100 (octoxynol) --.
Col. 13. line 43, change "Triton X-100" to -- TRITON X-100 (octoxynol) --.

Signed and Sealed this

Fifth Day of December, 2006

JON W. DUDAS
*Director of the United States Patent and Trademark Office*